(12) United States Patent
Ito

(10) Patent No.: US 8,372,950 B2
(45) Date of Patent: Feb. 12, 2013

(54) IGG BINDING PEPTIDE

(75) Inventor: Yuji Ito, Kagoshima (JP)

(73) Assignee: Kagoshima University, Kagoshima (JP)

( * ) Notice: Subject to any disclaimer, the term of this patent is extended or adjusted under 35 U.S.C. 154(b) by 620 days.

(21) Appl. No.: 12/312,268

(22) PCT Filed: Nov. 2, 2007

(86) PCT No.: PCT/JP2007/071754
§ 371 (c)(1), (2), (4) Date: May 1, 2009

(87) PCT Pub. No.: WO2008/054030
PCT Pub. Date: May 8, 2008

(65) Prior Publication Data
US 2010/0297606 A1    Nov. 25, 2010

(30) Foreign Application Priority Data

Nov. 2, 2006  (JP) .................. 2006-299566

(51) Int. Cl.
*C07K 7/00* (2006.01)
(52) U.S. Cl. ...................... 530/327; 530/326
(58) Field of Classification Search .............. 530/327, 530/326
See application file for complete search history.

(56) References Cited

U.S. PATENT DOCUMENTS

| 2003/0180718 A1* | 9/2003 | Pillutla et al. ............ 435/5 |
| 2003/0199671 A1* | 10/2003 | Rondon et al. ............ 530/317 |
| 2003/0233675 A1 | 12/2003 | Cao et al. |

FOREIGN PATENT DOCUMENTS

| WO | WO 02/057299 A2 | 7/2002 |
| WO | WO-02/086070 A2 | 10/2002 |
| WO | WO 03/035839 A2 | 5/2003 |

OTHER PUBLICATIONS

Abstract of Masatsugu (JP 2004-187563), Jul. 2004.*
Dias et al., "Protein Ligand Design: From Phage Display to Synthetic Protein Epitope Mimetics in Human Antibody Fc-Binding Peptidomimetics" J. Am. Chem. Soc., Feb. 2006. vol. 128, No. 8, pp. 2726-2732.
Itoh et al., "Random Peptide Library Kara no Hito Kotai IgG-Fc Tokuiteki Peptide no Design", Dai 127 Nenkai The Pharmaceutical Society of Japan TOYAMA2007 Summaries 4, Mar. 5, 2007, pp. 38.
Sakamoto et al., "Discovery and Characterization of a Peptide Motif that Specifically Recognizes a Non-native Conformation of Human IgG induced by Acidic pH Conditions", Journal of Biological Chemistry, vol. 284, No. 15, Apr. 10, 2009, pp. 9986-9993, XP002547442, ISSN: 0021-9258.
Supplementary European Search Report issued Mar. 22, 2010 in European Application No. 07831485.3
European Office Action issued Mar. 28, 2012 in European Application No. 07831485.3.

* cited by examiner

*Primary Examiner* — David Lukton
(74) *Attorney, Agent, or Firm* — Birch, Stewart, Kolasch & Birch, LLP

(57) ABSTRACT

The present invention provides a peptide capable of specifically binding to human IgG. In particular, the present invention relates to a human IgG binding peptide tag of 11 to 16 amino acids in length, comprising at least an amino acid sequence of the formula I:

C-$(X)_n$-W-X-X-X-W-$(X)_m$-C    (I)    (SEQ ID NO: 17)

wherein n and m are each an integer of 1 or more and the sum n+m is 4 or 5, wherein X-X-X in the formula I contains no cysteine residue, and
wherein said amino acid sequence satisfies either or both of a) and b):
 a) $(X)_n$-W in the formula I denotes Za-G-Y-W (SEQ ID NO: 18); and
 b) W-$(X)_m$ in the formula I denotes W-G-L-Zb (SEQ ID NO: 19)
wherein Za and Zb are each 0, 1, or more amino acid residues.

13 Claims, 18 Drawing Sheets
(4 of 18 Drawing Sheet(s) Filed in Color)

IGG BINDING PEPTIDE

This application is a 371 of PCT/JP2007/071754, filed Nov. 2, 2007, which claims foreign priority to JP 2006-299566, filed Nov. 2, 2006.

TECHNICAL FIELD

The present invention relates to a peptide having binding affinity for human IgG, and a method for detecting or purifying human IgG using the same.

The patent or application file contains at least one drawing executed in color. Copies of this patent or patent application publication with color drawing(s) will be provided by the office upon request and payment of the necessary fee.

BACKGROUND ART

More than 10 types of antibody are currently marketed in the U.S.A. as medicaments. Antibody drugs are attracting attention as molecular targeted drugs that can provide the highest certainty, contributing to the rapid enlargement of a field of new medicaments. Most antibody drugs that are currently under development or in use utilize immunoglobulin G (IgG) class antibodies. To date, an anti-Fc antibody or Protein A/G that specifically binds to the Fc region of an IgG antibody has often been used for detection or purification of an IgG antibody (Non-patent Documents 1 and 2). However, an anti-Fc antibody prepared by hybridoma technology or animal immunization has drawbacks such that it is not only expensive, but is also easily denatured upon labeling, for example. On the other hand, Protein A/G has drawbacks such that it is does not allow one to distinguish between IgGs derived from different organism species and it does not bind to human IgG3. Protein A/G is generally isolated from bacteria, leading to possible contamination with an endotoxin such as LPS. This poses a big problem upon the use of a Protein A column for antibody drug purification. Furthermore, antibody purification using a Protein A column can also lead to a problem such that antibody denaturation takes place due to acid when the antibody is eluded from the column using an acid solution, so that the yield drastically decreases or the quality of the thus purified antibody is lowered. It is very important to overcome such problems with antibody purification methods using an anti-IgG antibody or Protein A/G so as to develop a novel technique capable of specifically detecting and purifying human IgG.

Many IgG binding peptides that can be used for IgG purification have been reported so far. Fassina et al., have screened synthetic multimeric peptide libraries and then identified a Protein A peptide mimic that competes with Protein A for interactions with biotin-labeled immunoglobulin (Non-patent Documents 3 and 4). Also, Ehrlish et al., have isolated an Fc-binding peptide having a Protein A mimic sequence from an M13 phage display library displaying 12-mer or 7-mer linear peptides (Non-patent Document 5). Krook et al., have also reported identification of a Protein A peptide analog via reaction of a random peptide fUSE5 phage library displaying linear 10-mer peptides with IgG followed by elution with the use of Protein A (Non-patent Document 6). In 2005, Verdoliva et al., have reported a peptide motif from a cyclic synthetic peptide library, that recognizes regions near the hinge region of an IgG antibody and inhibits competitively the reaction of FcγRIII with IgG Fc (Non-patent Document 7). Moreover, Suzuki et al., have described peptides having a property of binding to IgG Fc fragments and disclosed a method for detecting IgG using the same (Patent Document 1). However, it cannot be said that all of these peptide motifs have sufficient IgG binding affinity as tags for purification and/or detection of an IgG antibody.

Meanwhile, in 2000, DeLano et al. have reported polypeptide sequences having binding affinity for the hinge region on a human IgG Fc fragment, such as the Fc-III peptide (DCAWHLGELVWCT; SEQ ID NO: 15), as a result of the use of an M13 phage library displaying cyclic peptides (Non-patent Document 8 and Patent Document 2). Furthermore, in 2006, Dias et al., have performed engineering so as to further stabilize the circularization of the peptide Fc-III (Non-patent Document 9). The peptide Fc-III of Delano et al., exhibited its binding affinity with a Kd value of 185 nM for an IgG antibody, but the Kd value exhibited by the improved peptide FcBP-2 of Dias et al. decreased to approximately 2 nM. It was thus suggested that the peptide FcBP-2 had an extremely strong binding force. However, the dissociation rate constant, koff, of FcBP-2 was found to be $10^{-2}$ sec$^{-1}$, as a result of analysis of kinetic parameters. Such dissociation rate is significantly faster than that of general koff ($10^{-3}$ to $10^{-5}$ Sec$^{-1}$) of an antibody. This indicates that even if the peptide FcBP-2 is used as a tag for purification or detection of an antibody, the dissociation rate is so fast that the bond between the peptide FcBP-2 and the antibody dissociate rapidly and the bond cannot be retained. Accordingly, FcBP-2 is inappropriate for use in human IgG purification and/or detection.

Patent Document 3 discloses various human IgG Fc binding peptides. However, Patent Document 3 does not disclose peptides appropriate for human IgG purification and/or detection, such as peptides capable of sufficiently retaining the bonds with any human IgG subclass and exhibiting no significant binding to IgGs of other organism species.

Patent Document 1: JP Patent Publication (Kokai) No. 2004-187563
Patent Document 2: International Publication WO01/045746 Pamphlet
Patent Document 3: International Publication WO02/086070 Pamphlet
Non-patent Document 1: Ey P. L., et al., Immunochemistry (1978) 15, p. 429-436
Non-patent Document 2: Akerstrom B., et al., J. Immunol., (1985) 135, p. 2589-2592
Non-patent Document 3: Fassina G., et al., J. Mol. Recognit. (1996) 9, p. 564-569
Non-patent Document 4: Fassina G., et al., J. Mol. Recognit. (1998) 11, p. 128-133
Non-patent Document 5: Ehrlich G. K. and Bailon P., J. Mol. Recognit. (1998) 11, p. 121-125
Non-patent Document 6: Krook M., Mosbach K., and Ramstrom O., J. Immunol. Methods (1998) 221, p. 151-157
Non-patent Document 7: Verdoliva A. et al., Chembiochem (2005) 6, p. 1242-1253
Non-patent Document 8: DeLano W. L., et al., Science (2000) 287, p. 1279-1283
Non-patent Document 9: Dias R. L., et al., J. Am. Chem. Soc. (2006) 128, p. 2726-2732

DISCLOSURE OF THE INVENTION

An object of the present invention is to provide a peptide having specific binding activity to human IgG, which can be appropriately used for purification or detection of human IgG.

As a result of concentrated studies to achieve the above object, the present inventors have discovered that short peptides with specific sequence patterns have species specificity such that they exhibit high binding activity to each subclass (IgG1 to IgG4) of a human IgG antibody without exhibiting significant binding to an antibody of a mouse, for example. It has also been shown that dissociation rates of these peptides are extremely slow in terms of the binding with human IgG antibody and the bonds can be more easily retained. Furthermore, it has been shown that the bonds between these peptides and the human IgG antibody can be significantly enhanced through acid treatment of a human IgG antibody. The present invention has been completed based on these findings.

Specifically, the present invention encompasses the following [1] to [12].

[1] A human IgG binding peptide tag of 11 to 16 amino acids in length, comprising at least an amino acid sequence of the formula I:

C-(X)$_n$-W-X-X-X-W-(X)$_m$-C  (I) (SEQ ID NO: 17)

wherein n and m are each an integer of 1 or more and the sum n+m is 4 or 5, wherein X-X-X in the formula I contains no cysteine residue, and
wherein the amino acid sequence satisfies either or both of a) and b):
  a) (X)$_n$-W in the formula I is Za-G-Y-W (SEQ ID NO: 18); and
  b) W-(X)$_m$ in the formula I is W-G-L-Zb (SEQ ID NO: 19) wherein Za and Zb are each 0, 1, or more amino acid residues.

In this peptide tag, more preferably, the amino acid sequence of the formula I satisfies both a) and b) above, that is:
  a) (X)$_n$-W in the formula I is Za-G-Y-W (SEQ ID NO: 18); and
  b) W-(X)$_m$ in the formula I is W-G-L-Zb (SEQ ID NO: 19) wherein Za and Zb are each 0, 1, or more amino acid residues.

Particularly preferred examples of the peptide tag of [1] above include peptide tags consisting of the amino acid sequences 1) to 11):

```
1)  CGYWRSEWGLC;       (SEQ ID NO: 1)
2)  CTGFWEREWGLC;      (SEQ ID NO: 2)
3)  CLYWPRLWGLC;       (SEQ ID NO: 3)
4)  CTGYWPKAWGLC;      (SEQ ID NO: 4)
5)  CYWAVRWGLLGC;      (SEQ ID NO: 5)
6)  CGYWADVWQIHC;      (SEQ ID NO: 6)
7)  GCGYWRSEWGLCG;     (SEQ ID NO: 7)
8)  GCTGFWEREWGLCG;    (SEQ ID NO: 8)
9)  GCTGYWPKAWGLCG;    (SEQ ID NO: 9)
10) GCGYWRSQWGLCG;     (SEQ ID NO: 10)
    and
11) GCTGYWPRAWGLCG.    (SEQ ID NO: 11)
```

In the peptide tag of [1] above, preferably, a disulfide bond is formed between two cysteine residues (C) in the formula I.

The peptide tag of [1] above preferably binds to acid-denatured human IgG

A labeling substance can be attached to the peptide tag of [1] above.

[2] A recombinant bacteriophage displaying the peptide tag of [1] above.

[3] A fusion protein, containing a protein linked to the peptide tag of [1] above.

[4] A solid phase support, on which the peptide tag of [1] above is immobilized.

[5] DNA encoding the peptide tag of [1] above.

[6] A vector comprising DNA of [5] above.

[7] A transformant comprising the vector of [6] above.

[8] A method for detecting human IgG or an Fc region-containing fragment thereof in a sample, comprising the steps a) to c):
  a) acid treating a sample;
  b) contacting the acid-treated sample with the peptide tag of [1] above; and
  c) measuring the level of binding produced in the step b) between the peptide tag and human IgG or an Fc region-containing fragment thereof.

In the detection method, the level of binding may be appropriately measured by surface plasmon resonance analysis.

[9] A method for purifying human IgG or an Fc region-containing fragment thereof in a sample, comprising the steps a) and b):
  a) contacting the peptide tag of [1] above with an acid-treated sample, thereby binding human IgG or an Fc region-containing fragment thereof in the sample to the peptide tag; and
  b) separating the human IgG or the Fc region-containing fragment thereof, which is bound to the peptide tag in the step a), from the sample.

[10] A method for removing an acid-denatured human IgG or Fc region-containing fragment thereof from a sample, comprising the steps a) and b):
  a) contacting the peptide tag of [1] above with a sample; and
  b) removing human IgG or an Fc region-containing fragment thereof, which is bound to the peptide tag in the step a), from the sample.

[11] A method for purifying a protein, comprising the steps a) to c):
  a) producing a fusion protein containing a protein linked to the peptide tag of [1] above and then preparing a sample containing the fusion protein;
  b) contacting the sample prepared by the step a) with acid-treated human IgG or an Fc region-containing fragment thereof, thereby binding the fusion protein to the human IgG or Fc region-containing fragment thereof; and
  c) separating the fusion protein, which is bound to the human IgG or Fc region-containing fragment thereof in the step b), from the sample.

[12] A kit for detecting or purifying human IgG or an human IgG Fc region-containing fragment, comprising at least one selected from the group consisting of the peptide tag of [1] above, the recombinant bacteriophage of [2] above, the solid phase support of [4] above, the vector of [6] above, and the transformant of [7] above.

The peptide tag of the present invention can specifically bind to human IgG and can particularly bind successfully to acid-denatured human IgG.

The disclosure of Japanese Patent Application No. 2006-299566, of which the present application claims the priority, is included herein.

BRIEF DESCRIPTION OF THE DRAWINGS

FIG. 8A shows the results of surface plasmon resonance analysis of the binding between human IgG-specific synthetic peptide IMGpep-1 and human IgG. FIG. 8B shows the results of surface plasmon resonance analysis of the binding between human IgG-specific synthetic peptide IMGpep-1E6Q and human IgG FIG. 8C shows the results of surface plasmon resonance analysis of the binding between human IgG-specific synthetic peptide IMGpep-4 and human IgG. FIG. 8D shows the results of surface plasmon resonance analysis of the binding between human IgG-specific synthetic peptide IMGpep-4K6R and human IgG.

In FIG. 11, a continuous line indicates the level of human IgG bound on an Fc-III-immobilized sensor chip and a broken line indicates the level of human IgG bound on an IMGpep-4K6R-immobilized sensor chip.

In FIG. 12, open (white) bars, closed (black) bars, and oblique-line bars indicate samples acid-treated at an incubation temperature of 20° C., 30° C., and 40° C., respectively.

In FIG. 13, a continuous line indicates an acid-treated anti-HER2 human IgG antibody sample, a broken line indicates an untreated anti-HER2 human IgG antibody sample (Herceptin), and a dashed line indicates BSA.

FIG. 15A: Untreated human IgG (anti-IL-6 receptor human antibody, MRA). FIG. 15B: Acid-treated human IgG (MRA) (treated at pH 2.7, 30° C., 10 minutes). FIG. 15C: Acid-denatured MRA purified through a biotinylated IMGpep-4K6R-immobilized column. FIG. 15D: A flow-through fraction (MRA remained undenatured) obtained via application of acid-treated human IgG (MRA) (treated at pH 2.7, 30° C., 10 minutes) to an IMGPep-4K6R-immobilized column.

In FIG. 18, K6R(N) denotes non-acid-treated human IgG as detected with the IMGpep-4K6R peptide; Fc-III(N) denotes non-acid-treated human IgG, as detected with Fc-III peptide; K6R(A) denotes acid-treated human IgG (incubated at pH 2.8 and 40° C. for 10 minutes), as detected with the IMGpep-4K6R peptide; and CS(N) denotes non-acid-treated human IgG, as detected with the IMGpep-1CS peptide.

BEST MODE FOR CARRYING OUT THE INVENTION

Figure 1:
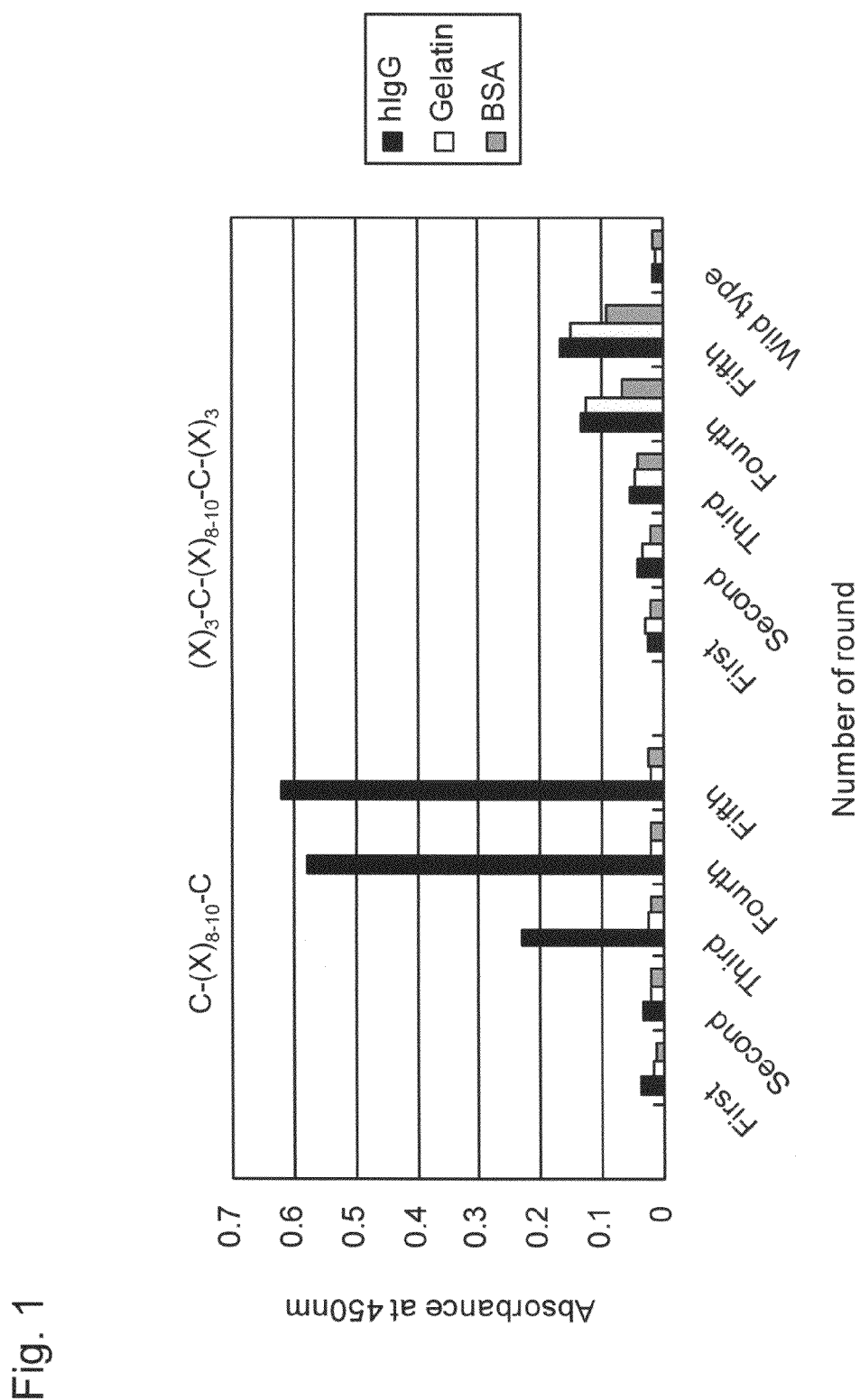
FIG. 1 shows the results of enrichment of IgG-specific phages (closed (black) bar) by biopanning against a human IgG antibody. The bars indicate, from the left, per each round, phages exhibiting properties of binding to hIgG, gelatin, and BSA, respectively.

The present invention will be further illustrated specifically with reference to examples. However, the technical scope of the present invention is not limited by the following examples.

The present invention will be described specifically as follows.

1. Peptide Tag According to the Present Invention

The present invention relates to a peptide tag that specifically binds to the Fc region of human immunoglobulin G (IgG) and particularly to the Fc region of acid-denatured human immunoglobulin G, and a method for detecting, purifying, or removing human IgG using the peptide tag.

In the present invention, the term "peptide tag" refers to a peptide to be used for detection, capturing, purification (including enrichment and the like), separation and removal, and the like of a target molecule (within the context of the present invention, i.e., human IgG or an Fc region-containing fragment thereof or, e.g., labeled products thereof) with the use of the binding specificity of the peptide tag to the target molecule.

The peptide tag according to the present invention is a peptide with a short chain length, containing a peptide sequence or an analogous sequence thereto, wherein cysteine residues are placed one by one on both sides of a 9- or 10-amino-acid-long sequence comprising the sequence (G-Y-W-X-X-X-W-G-L) (SEQ ID NO: 20) in which three any (arbitrary) amino acid residues are sandwiched between the common motifs, 3-amino acid sequences G-Y-W and W-G-L. The term "analogous sequence" refers to an amino acid sequence that has a high homology with the above peptide sequence, and in which at least either one motif sequence of G-Y-W or W-G-L and the above sequence pattern W-X-X-X-W (SEQ ID NO: 21) are conserved. Examples of such analogous sequence include an amino acid sequence C-$(X)_{0-2}$-(F or Y)-W-X-X-X-W-(G or Q)-(L or I)-$(X)_{0-2}$-C (SEQ ID NO: 22). Here, $(X)_{0-2}$ is a sequence of 0 to 2 consecutive any amino acid residues X.

More generally, the IgG binding peptide tag according to the present invention is defined as a peptide comprising at least an amino acid sequence of the following formula I:

$$C\text{-}(X)_n\text{-}W\text{-}X\text{-}X\text{-}X\text{-}W\text{-}(X)_m\text{-}C \text{ (SEQ ID NO: 17)} \qquad (I)$$

wherein n and m are each an integer of 1 or more and the sum n+m is 4 or 5, wherein X-X-X in the formula I contains no cysteine residue, and
wherein said amino acid sequence satisfies either or both of the following a) and b):
  a) $(X)_n$-W in formula I is Za-G-Y-W (SEQ ID NO: 18)
  b) W-$(X)_m$ in formula I is W-G-L-Zb (SEQ ID NO: 19)
wherein Za and Zb are each 0, 1, or more (specifically, up to 2 amino acid residues so as to satisfy n+m=4 or 5) amino acid residues (preferably, excluding cysteine residue). As the peptide tag, 11- to 16-amino-acid-long peptides and preferably 11- to 14-amino-acid-long peptides are preferred.

In addition, X-X-X in formula I is preferably a 3-amino acid sequence containing no cysteine residue. Furthermore, X-X-X in formula I is preferably a 3-amino acid sequence containing no tryptophan residue.

As a rule, amino acid sequences (e.g., formula I above) described in this description are denoted with general three letter codes or one letter codes for amino acids. That is, for example, in formula I above, C denotes a cysteine residue (Cys) and W denotes a tryptophan residue (Trp). Also, X denotes any one amino acid residue. $(X)_n$ and $(X)_m$ denote a sequence of "n" number of consecutive any amino acid residues X and a sequence of "m" number of consecutive any amino acid residues X, respectively. Also, X-X-X denotes a sequence of three consecutive amino acid residues. Moreover, G denotes a glycine residue (Gly), Y denotes a tyrosine residue (Tyr), and L denotes a leucine residue (Leu).

A more preferred peptide tag of the present invention is as follows:
a human IgG binding peptide tag comprising an amino acid sequence of the following formula II,

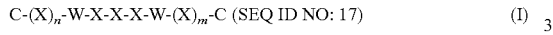

$$(X)_p\text{-}C\text{-}(X)_n\text{-}W\text{-}X\text{-}X\text{-}X\text{-}W\text{-}(X)_m\text{-}C\text{-}(X)_q \qquad (II) \text{ (SEQ ID NO: 23)}$$

wherein p=0 or 1, n and m are each an integer of 1 or more, n+m=4 or 5, and q=0 or 1, and X-X-X in formula II contains no cysteine residue; and
wherein the amino acid sequence satisfies either or both of the following a) and b):
  a) $(X)_n$-W in formula II is Za-G-Y-W (SEQ ID NO: 18); and
  b) W-$(X)_m$ in formula II is W-G-L-Zb (SEQ ID NO: 19)
wherein Za and a are each 0, 1, or more amino acid residues (preferably, excluding cysteine residue).

$(X)_p$ and/or $(X)_q$ in formula II may be absent (i.e.; when p,q=0). Alternatively, $(X)_p$ and/or $(X)_q$ in formula II is preferably one glycine residue (G) each. Particularly preferably, $(X)_p$ and/or $(X)_q$ in formula II comprises any amino acid residues other than a cysteine residue.

The peptide tag of the present invention represented by formula I or II can exhibit higher binding affinity for human IgG Fc region, when it contains both Za-G-Y-W (SEQ ID NO: 18) and W-G-L-Zb (SEQ ID NO: 19) sequences as described in a) and b) above.

Particularly appropriate examples of the peptide tag of the present invention include peptide tags comprising the following amino acid sequences. These amino acid sequences are denoted with one letter codes for amino acids.

| | |
|---|---|
| CGYWRSEWGLC | (SEQ ID NO: 1) |
| CTGFWEREWGLC | (SEQ ID NO: 2) |
| CLYWPRLWGLC | (SEQ ID NO: 3) |
| CTGYWPKAWGLC | (SEQ ID NO: 4) |
| CYWAVRWGLLGC | (SEQ ID NO: 5) |
| CGYWADVWQIHC | (SEQ ID NO: 6) |
| GCGYWRSEWGLCG | (SEQ ID NO: 7) |
| GCTGFWEREWGLCG | (SEQ ID NO: 8) |
| GCTGYWPKAWGLCG | (SEQ ID NO: 9) |
| GCGYWRSQWGLCG | (SEQ ID NO: 10) |
| GCTGYWPRAWGLCG | (SEQ ID NO: 11) |

In the peptide tag of the present invention, preferably, a disulfide bond is formed between two cysteine residues (C) contained in the sequence of the peptide tag. A disulfide bond is formed under non-reducing conditions (e.g., under the presence of 10 mM to 50 mM oxidized glutathione), but is not formed under reducing conditions (e.g., under the presence of 10 mM to 50 mM dithiothreitol). The disulfide bond formation results in the formation of a compact cyclic structure in the peptide tag of the present invention.

The peptide tag of the present invention exhibits high binding activity to, particularly, acid-denatured Fc region of an human immunoglobulin G (IgG) antibody. The peptide tag is capable of strongly binding to such an acid-denatured form of human IgG (whole antibody) or an Fc region-containing fragment thereof.

Human IgG is digested by papain or the like to give two Fab fragments (arm portions containing variable and constant regions) and an Fc fragment (trunk portion containing constant regions). The Fc fragment from IgG antibody is one of antibody fragments obtained via cleavage of IgG with papain enzyme, and composed of carboxyl-terminal approximately half fragments (comprised of CH2 domains and CH3 domains that are constant regions) of two H chains, which are linked via two disulfide bonds each other. Meanwhile, the term "Fc region" in the present invention refers to a region consisting of CH2 domain and CH3 domain within H chain, which is contained in the Fc fragment. In addition, the term "Fc region-containing fragment of human IgG" herein may be a fragment obtained via digestion of human IgG with protease (typically, a fragment produced by papain or trypsin digestion) or a portion of human IgG which contains the Fc region of human IgG, but is not a fragment obtained via digestion with protease. The "Fc region-containing fragment of human IgG" can be a portion of IgG that contains 1, 2, or more H-chain-derived fragments, each consisting of CH2 domain and CH3 domain.

In the context of the present invention, the term "acid-denatured human immunoglobulin G (IgG)" refers to human immunoglobulin G having specific (special) conformation because of conformational (structural) denaturation of a normal IgG antibody as a result of acid treatment, or human immunoglobulin G having a conformation equivalent to such specific conformation regardless of the presence or absence of acid treatment. In the acid-denatured human immunoglobulin G (IgG), most of the secondary structures such as β-sheet structures are preferably retained while randomized structures are partially recognized. Specifically, it seems that the acid-denatured human immunoglobulin G (IgG) has a conformation in an intermediate state of denaturation. Here, the term "acid treatment" refers to, but is not limited to, exposure of immunoglobulin G under conditions of preferably pH 3.5 or less, such as pH 1.5 to 2.7, and more preferably under conditions of pH 1.5 to 2.1. The acid treatment is preferably carried out by incubating immunoglobulin G, under the above-mentioned acidic conditions, at 4° C. to 50° C., preferably 20° C. to 50° C., and more preferably 30° C. to 40° C. The step of acid treatment can take 1 minute to 3 minutes or more, such as 5 minutes to 10 minutes, for example. An IgG-containing solution can be prepared under such acidic conditions, and the pH of the solution subsequently can also be neutralized by the addition of a basic solution such as Tris. For example, acid treatment can be carried out by adjusting the pH of a solution containing an antibody to pH 1.5 and then incubating the solution for 5 minutes, and the pH of the solution subsequently can be neutralized (but not limited thereto). Furthermore, human immunoglobulin G having a denatured conformation equivalent to that resulting from acid treatment may also be generated by, as a nonlimiting example, freezing or refrigerating human IgG, or long storage of human IgG under neutral pH conditions, or alternatively generated by introducing a mutation into human IgG or adding or removing sugar chains. The acid-denatured human immunoglobulin G in the present invention may or may not retain its antigen-binding activity. General human IgG preparations, such as commercially available polyclonal human IgG antibody products can contain some amounts of acid-denatured human immunoglobulin G. Particularly, a purified human IgG product eluted using an acid eluting solution from a Protein A column or the like, is generally contaminated by acid-denatured human immunoglobulin G.

The peptide tag of the present invention exhibits high binding activity to any of IgG1, IgG2, IgG3, and IgG4, which are human IgG subclasses (isotypes). The peptide tag of the present invention exhibits particularly high binding activity to each subclass of acid-denatured human IgG. The peptide tag of the present invention also exhibits high binding activity to oligomers (e.g., dimers and trimers) of acid-denatured human IgG.

Moreover, preferably, the peptide tag of the present invention does not exhibit any binding activity to human immunoglobulin classes (e.g., IgA, IgE, and IgM) other than IgG. Preferably, the peptide tag of the present invention does not also exhibit any binding activity to various immunoglobulin classes and subclasses of non-human animals (e.g., mice). Therefore, the peptide tag of the present invention can bind very specifically to particularly acid-denatured human IgG or the Fc region thereof. In addition, the peptide tag of the present invention competitively inhibits the binding of Protein A to human IgG, so that it is thought to bind to around the junction of CH2 domain and CH3 domain within the IgG Fc region that is the binding site for Protein A.

The peptide tag of the present invention can be prepared by any methods for chemical synthesis of peptides, such as liquid phase synthesis, solid phase synthesis, and an Fmoc method, which are well-known to persons skilled in the art (see Kelley et al., Genetics Engineering Principles and Methods, Setlow, J. K. eds., Plenum Press NY. (1990) Vol. 12, p. 1-19; Stewart et al., Solid-Phase Peptide Synthesis (1989) W.H. Freeman Co.; Houghten, Proc. Natl. Acad. Sci. U.S.A. (1985) 82: p. 5132; and "*Shin Seikagaku Jikken Ko-za* 1 (New Biochemical Experiment Lecture 1) Protein IV" (1992) Ed., The Japanese Biochemical Society, TOKYO KAGAKU DOZIN CO., LTD, for example). Peptide synthesis is also generally carried out using an automated peptide synthesizer. Alternatively, the peptide may also be produced by a recombinant method, a phage display method, or the like using a DNA encoding the peptide tag of the present invention. For example, the peptide tag of interest can be produced by inserting a DNA encoding the amino acid sequence of the peptide tag of the present invention into an expression vector, introducing it into host cells, and then culturing the cells. The thus produced peptide tag can further be recovered or purified by a conventional method such as gel chromatography, ion column chromatography, affinity chromatography, reverse phase column chromatography, ammonium sulfate fractionation, difference-in-solubility-based fractionation using alcohol or the like, and immunoadsorption.

The peptide tag of the present invention is preferably caused to form a disulfide bond under non-reducing conditions. For example, the thus prepared peptide tag of the present invention is left to stand in a buffer with pH 8 to expose the peptide to air oxidation, so as to cause disulfide bond formation.

A labeling substance can be attached to the peptide tag of the present invention. The peptide tag to which a labeling substance has been attached or human IgG bound thereto can be easily detected with high sensitivity. Examples of a labeling substance include, but are not limited to, biotin, iminobiotin, digoxigenin, fluorescent proteins, fluorescent dyes, chemoluminescent dyes, enzymes, and radioisotopes. Specific examples of the labeling substance include biotin, iminobiotin, digoxigenin, green fluorescent protein (GFP), yellow fluorescent protein (YFP), aequorin, and fluorescein. Methods for labeling proteins using these labeling substances are well-known to persons skilled in the art. For example, biotin can also be attached to the peptide tag of the present invention via biotinylation modification using a commercially available reagent such as Sulfo-NHS-LC-Biotin (Pierce). A labeling substance may also be attached to the peptide tag of the present invention via a linker. This linker can be any substance capable of constituting a link between a protein and a peptide, such as a peptide, fatty acid, and a fatty acid ester. Such linker may be inserted between the peptide tag and a protein as a spacer for avoiding the inhibition of formation of protein conformation, or as a cleavable link containing a protease recognition site.

The present invention also relates to a recombinant bacteriophage displaying the peptide tag of the present invention. Such recombinant bacteriophage can be prepared using a phage display method known to persons skilled in the art. For example, various DNAs encoding the peptide tags of the present invention are inserted into vectors for construction of phage display libraries such as a T7 phage vector, the vectors are packaged into bacteriophages, and then bacteriophages are propagated, so that the thus obtained recombinant bacteriophages can display the peptide tags of the present invention.

The present invention also relates to a fusion protein containing a protein linked to the peptide tag of the present invention. The peptide tag of the present invention can be ligated (attached) to any protein, preferably at the N-terminus or C-terminus, for using as an affinity tag for detection and/or purification of the protein. In the fusion protein, the peptide tag of the present invention may be linked to a protein of interest via a linker. This linker may be any substance that can constitute a link between a protein and the peptide, such as a cleavable link containing a protease recognition site. These fusion proteins can be easily isolated using the property of specific binding of the peptide tag of the present invention to human IgG or the Fc region thereof (particularly, acid-denatured human IgG or the Fc region thereof).

The above-mentioned fusion protein can be prepared by a genetic recombination method well-known to persons skilled in the art, for example. For example, a gene encoding the protein and a DNA encoding the peptide tag can be inserted in the proper reading frame into an expression vector or expression cassette, and introduced into host cells, cultured for expression of the gene, and the thus produced protein can be recovered. Examples of a protein to be fused to the peptide tag of the present invention include, but are not limited to: enzymes such as amyloglycosidase, amylase, invertase, isoamylase, protease, papain, pepsin, rennin, cellulase, pectinase, lipase, lactase, glucose oxidase, lysozyme, glucose isomerase, chymotrypsin, trypsin, cytochrome, seaprose, serratio peptidase, hyaluronidase, bromelain, urokinase, hemocoagulase, thermolysin, and urease; cytokines such as interferon and interleukin; hormones such as insulin, glucagon, secretin, gastrin, cholecystokinin, oxytocin, vasopressin, growth hormone, thyroid-stimulating hormone, prolactin, luteinizing hormone, follicle-stimulating hormone, adrenocorticotropic hormone, thyrotropin-releasing hormone, luteinizing hormone-releasing hormone, adrenocorticotropin-releasing hormone, growth hormone-releasing hormone, and somatostatin; opioid peptides such as endorphin, enkephalin, and dynorphin; blood coagulation factors such as fibrinogen and prothrombin; protease inhibitors such as SSI; and albumin, globulin, globin, keratin, and collagen.

The present invention also relates to a solid-phase support on which the peptide tag of the present invention is immobilized. Examples of an appropriate solid-phase support to be used for immobilization of the peptide tag include, but are not limited to, polystyrene, polyethylene, polypropylene, polyester, polyacrylonitrile, styrene-butadiene copolymer, (meth) acrylic ester polymer, resins such as a fluorocarbon resin and a silica gel resin, macromolecular substances such as cross-linked dextran, polysaccharide, and agarose, and substrates such as glass, metal, a magnetic substance, and a combination thereof. The form of such solid-phase support may be any form, such as a tray, a sphere, a fiber, a particle, a bar, a disk, a vessel, a cell, a microplate, a test tube, a membrane, gel, and a chip (e.g., sensor chip). Specific examples of such support include magnetic beads, glass beads, polystyrene beads, Sepharose beads, polystyrene plates, glass plates, and polystyrene tubes. The peptide of the present invention can be immobilized on these solid-phase supports using methods well-known to persons skilled in the art, such as a physical adsorption method, a covalent bonding method, and an ion binding method.

The thus obtained solid-phase support on which the peptide tag of the present invention is immobilized can be preferably used for detection, capturing, purification, separation, or the like of human IgG and can be particularly preferably used for detection, capturing, purification, or removal of acid-denatured human IgG, but not limited thereto. For example, such a solid-phase support on which the peptide tag of the present invention is immobilized can be used for detection, capturing, purification, or separation of human IgG with high efficiency after filling a column such as an affinity chromatography column with the support. In a more specific example, human IgG can be bound with high efficiency to the peptide tag on the solid-phase support by acid treating a sample containing human IgG and then contacting the resultant with the solid-phase support. Alternatively, human IgG can also be purified with more uniform quality by contacting a sample containing human IgG with such a solid-phase support to specifically capture acid-denatured human IgG in the sample, and then removing the captured one from the sample. The present invention also encompasses the above-described column filled with the solid-phase support of the present invention.

The present invention also relates to a nucleic acid (particularly, DNA) encoding the peptide tag of the present invention. In particular, DNAs encoding the amino acid sequences of SEQ ID NOS: 1 to 11 are preferred embodiments of the present invention, for example. Such a DNA can be inserted and ligated into an appropriate vector for easily handing in the form of a recombinant vector. A vector into which a DNA encoding the peptide tag of the present invention is inserted is not particularly limited, as long as it is replicable in host cells. Examples of such vector include virus vectors such as a phage vector, phagemid vectors, cosmid vectors, and plasmid vectors. The present invention also provides such vector comprising a DNA encoding the peptide tag.

Examples of a phage vector include, but are not limited to, T7 phage display vectors (e.g., T7Select10-3b, T7Select1-1b, T7Select1-2a, T7Select1-2b, and T7Select1-2c (Novagen)) and λ phage vectors (e.g., Charon4A, Charon21A, EMBL3, EMBL4, λgt10, λgt11, λZAP, and λZAPII). Also, any animal virus vectors such as retrovirus or vaccinia virus and any insect virus vectors such as baculovirus can be used. Examples of a cosmid vector include, but are not limited to, Lorist 6, Charomid9-20, and Charomid9-42.

Examples of a plasmid vector include, but are not limited to, plasmids derived from *Escherichia coli* (e.g., pET22b(+), pBR322, pBR325, pUC118, pUC119, pUC18, pUC19, and pBluescript), plasmids derived from *Bacillus subtilis* (e.g., pUB110 and pTP5), and plasmids derived from yeast (e.g., YEp13 and YCp50).

Within the scope of the vector containing the DNA encoding the peptide tag of the present invention, a vector for preparation of a fusion protein to which the peptide tag of the present invention is attached as a labeling tag, that contains a DNA fragment encoding the peptide tag of the present invention and has a restriction site for insertion of a gene encoding another protein is also included.

An example of a method that is employed for insertion of a DNA encoding the peptide tag into a vector involves, first, digesting a purified vector DNA with an appropriate restriction enzyme and then inserting in-frame and ligating a DNA encoding the peptide tag of the present invention to the thus exposed restriction enzyme site.

The recombinant vector of the present invention is also preferably constructed as a recombinant expression vector, so that a DNA encoding the peptide tag is expressed as a peptide having preferable activity within a host. For construction of such recombinant expression vector, commercially available various expression vectors can be used corresponding to various host organisms. To an expression vector, in general, useful sequences such as cis elements including a selectable marker, a reporter gene, a polylinker, and an enhancer, and a poly A additional signal, and a ribosome binding sequence (SD sequence) can be ligated if necessary, in addition to various elements essential for expression in host organisms, such as a transcription promoter, a terminator, and a ribosome binding site. As a selectable marker, a dihydrofolate reductase gene, an ampicillin resistance gene, a neomycin resistance gene, or the like can be used.

To the above-described vector, a DNA encoding the peptide tag of the present invention is preferably ligated to a position in an orientation so as to enable appropriate expression. When the peptide tag of the present invention is expressed by a recombinant method, a vector is preferably an expression vector containing a promoter.

According to the present invention, the peptide tag of the present invention can be produced by preparing a transformant (e.g., transformed single cells, calli, or tissues) via introduction of a vector that contains a DNA encoding the peptide tag, culturing the transformant under conditions where the transformant can be expressed, and then recovering the peptide tag of the present invention produced in cultured cells or culture solutions. The present invention also encompasses such transformant and a method for producing the peptide of the present invention with the use of such transformant.

Any host cells can be used for transformation, such as bacteria (e.g., *Escherichia coli* and *Bacillus subtilis*), yeast cells, insect cells, animal cells (e.g., mammalian cells), and plant cells.

For transformation, generally employed techniques, such as a calcium phosphate method, an electroporation method, a lipofection method, a particle gun method, and a PEG method can be applied. A transformant can be selected according to a conventional method. Generally a transformant is selected based on a selection marker or a reporter protein incorporated in a recombinant vector used.

The transformant of the present invention is cultured according to a method generally employed for culturing host organisms. As a medium for culturing the transformant obtained using a microorganism as a host such as *Escherichia coli* or yeast cells, either a natural or synthetic medium may be used as long as it contains carbon sources, nitrogen sources, inorganic salts, and the like assimilable by the host microorganism and is capable of efficiently culturing the transformant. For example, antibiotics such as ampicillin or tetracycline may also be added to a medium, if necessary.

When a host organism (microorganism) transformed with an expression vector containing an inducible promoter used therein is cultured, an inducer may be added to a medium as needed. For example, when a microorganism transformed with an expression vector containing a Lac promoter used therein is cultured, isopropyl-1-thio-β-D-galactoside (IPTG) or the like can be added to the medium. When a microorganism transformed with an expression vector containing a trp promoter used therein is cultured, indoleacetic acid (IAA) or the like can be added to the medium.

Culture conditions are not particularly limited. Host organisms are preferably cultured under conditions suitable for the host organisms to be used for transformation.

If the thus expressed peptide tag of the present invention is produced within host cells after culturing the cells, the cells are disrupted. On the other hand, if the peptide tag of the present invention is secreted extracellularly, the culture solution is directly used or the cells are removed by centrifugation or the like and then a culture supernatant is obtained. The thus obtained solution contains the peptide tag of the present invention. In the present invention, the peptide tag of the present invention may also be produced using a cell-free translation system instead of transformation.

The term "cell-free translation system" refers to an in vitro transcription-translation system or an in vitro translation system constructed in a test tube or the like through addition of a reagent such as amino acids required for translation to a suspension obtained by mechanically disrupting the cell structure of a host organism, such as *Escherichia coli*. As a cell-free translation system, advantageously usable kits are marketed.

The thus produced peptide tag of the present invention can be isolated and purified from the above culture (cell lysates, culture solutions, or culture supernatants thereof) or the solution of a cell-free translation system by an independent or an adequate combination of general biochemical methods that are employed for peptide isolation and purification, such as ammonium sulfate precipitation, gel chromatography, ion exchange chromatography, affinity chromatography, and reverse phase chromatography. However, if necessary, culture supernatants or lysate supernatants that are collected or concentrated by centrifugation or by the use of an ultrafiltration filter, or solutions obtained by subjecting such supernatants to dialysis after ammonium sulfate fractionation can be directly used for tests or the like concerning the property of binding to IgG.

2. Property of Binding of Peptide Tag to IgG and Detection, Purification, Capturing, or Separation of Human IgG Using the Same According to the present invention, human IgG or an Fc region-containing fragment thereof in a sample can be detected, captured, purified, separated, or the like with high sensitivity by the use of the peptide tag of the present invention capable of specifically binding to human IgG Fc region and particularly to acid-denatured human IgG Fc region. In particular, according to the present invention, acid-denatured human IgG or an Fc region-containing fragment thereof in a sample can be detected, captured, purified, removed, or the like with high sensitivity by the use of peptide tag of the present invention.

The binding state of the peptide tag of the present invention to human IgG or an Fc region-containing fragment thereof can be indicated by means of dissociation constant (Kd), affinity constant (Ka), association rate constant (ka), dissociation rate constant (kd), or the like as an indicator.

Dissociation constant (Kd) and affinity constant (Ka) are indicators indicating binding affinity; that is, the binding intensity, between two molecules in equilibrium. Dissociation constant (Kd) is the reciprocal of affinity constant (Ka). The lower the value of dissociation constant (Kd), the stronger the binding. On the other hand, the rate of an association-dissociation reaction between two molecules in equilibrium is represented by association rate constant, ka, (also denoted as "kon") and dissociation rate constant, kd, (also denoted as "koff") that are calculated by kinetic analysis. Association rate constant (ka) is the reciprocal of dissociation rate constant (kd). The higher the value of dissociation rate constant (ka), the more rapid the dissociation and the briefer the retention of the binding state. Therefore, values of dissociation constant (Kd) equivalent to each other indicate a case in which association and dissociation proceed slowly (both "ka" and "kd" values are low) or a case in which association and dissociation proceed rapidly (both "ka" and "kd" values are high). The two cases completely differ from each other in terms of the state of binding retention.

These dissociation constant (Kd), affinity constant (Ka), association rate constant (ka), dissociation rate constant (kd), and the like representing the binding state of the peptide tag of the present invention to human IgG can be determined using any method for measuring molecular interaction, which is well-known to persons skilled in the art. Particularly in the present invention, the binding state of the peptide tag of the present invention to human IgG (or a Fc region-containing fragment of human IgG) is preferably measured by surface plasmon resonance spectrum analysis. Surface plasmon resonance spectrum analysis can be carried out using but not limited to, a BIACORE system (BIACORE) that is a biosensor (biological molecular interaction analyzer), including BIACORE2000.

The BIACORE system is an analyzer capable of monitoring in real-time the interaction (association and dissociation) between biological molecules based on the principle of surface plasmon resonance spectrum (SPR) without labeling. Regarding the principle of surface plasmon resonance, many detailed descriptive literatures have been published (e.g., Setsuko Hashimoto, "Description of Biological Molecular Interaction Using Surface Plasmon Resonance," Analysis, May, 1997, (1997), published by The Japan Society for Analytical Chemistry, pp. 362-368). The principle employed in this analyzer is briefly explained as follows. A substance is caused to associate/dissociate on a gold film and then changes in the refractive index of the reflected light occurred with the mass changes on the chip due to the association/dissociation is measured, so that the level of the substance bound onto the gold film was calculated. More specifically, a glass substrate on which a gold film has been adhered, that is referred to as a sensor chip, is placed within the analyzer, such that the sensor chip is exposed to the flow of a sample or a reagent in channels through which the sample or the reagent is injected. Polarized light at 760 nm is focused in a wedge-shape on the sensor chip using a prism or the like while injecting a sample or the like through the channels, and then reflected on the gold film. The refractive index of the reflected light is monitored, so that a change in the angle is observed in the surface plasmon resonance spectrum in proportion to a change in the level of a substance bound onto the gold film. In the BIACORE system, first, a ligand is injected through the channels so that the ligand is immobilized on the gold film of a sensor chip in advance. Subsequently, sites to which no ligand has been bound are blocked. The refractive index of reflected light is monitored with time while injecting a subject substance (analyte) (to be subjected to examination of association/dissociation reaction with the ligand) through the channels. Based on the resulting level of change, the level of binding between the ligand and the analyte can be calculated. For the system, a change in the angle of 0.1° as shown in the surface plasmon resonance spectrum is defined as 1000 response units (RUs). Changes in the refractive index of reflected light are expressed based on the value of RU (response unit). Here, 1 response unit (RU) corresponds to a change in the mass of 1 pg/1 mm$^2$ on the sensor chip surface. Specifically, the amount of bound substance to the gold film on a sensor chip can be calculated using the difference between the RU found at a time point before binding of the substance (before addition of the substance) and the RU found at the time point of completion of the binding. Accordingly, with the use of the BIACORE system, the level of binding between a ligand (e.g., the peptide tag of the present invention) and an analyte (e.g., IgG antibody in a sample) can be determined as the RU value per 1 mm$^2$ sensor chip. The level of the binding (RU value) corresponds to the binding ability of the analyte to the ligand. In surface plasmon resonance spectrum analysis, association rate constant (ka) and dissociation rate constant (kd) can be determined from the initial rate based on the association curve representing changes in binding ability (level of binding). Furthermore, dissociation constant (Kd) and affinity constant (Ka) can be determined from the values of association rate constant (ka) and dissociation rate constant (kd) (Kd=kd/ka). Analysis software BIA evaluation (Biacore) is generally used for this analysis.

Sensor chips that can be used in a BIACORE system are varied in types depending on substances (ligands) to be immobilized on the chips, immobilization methods, purposes for use, and the like. Examples of such sensor chip include, in addition to the most standard CM5 (CM5 is provided with a gold film (typically, 50 nm) adhered onto a glass surface and an dextran layer (typically, 100 nm) further present thereon. A ligand is Immobilized thereto via an amino group, a thiol group, or an aldehyde group), CM4, CM3, C1, SA, Series S, NTA, L1, and HPA.

In the present invention, a ligand is immobilized on a sensor chip according to the manufacturer's instruction of a BIACORE system, for example. For example, a ligand can be immobilized via amine coupling onto a sensor chip CM5. For example, a method for the immobilization may be carried out by either a physical adsorption or adsorption via covalent binding. Immobilization can be carried out by binding a biotinylated peptide tag to streptavidin on a sensor chip SA, for example. As an example, when a sensor chip SA (BIACORE) is used as a sensor chip, a biotinylated peptide (50 μM) is injected through channels (e.g., flow cells) and then the peptide is immobilized on streptavidin immobilized in dextran on the sensor chip. Subsequently, for example, a sample (analyte solution) containing acid-denatured human IgG is injected through the channels, and then the level of binding between the peptide tag (ligand) on the chip and human IgG or the like (analyte) in the sample is calculated. An example of measurement conditions for BIACORE 2000 that can be used for the analysis is, but not limited to, as shown below:

Running buffer: HBS-T buffer;
Flow rate: 10 μl/minute;
Reaction temperature: 25° C.;
Regeneration solution: 0.2 M glycine-HCl buffer (pH 2.7);
Level of ligand immobilized: 400 RU to 1000 RU; and
pH upon immobilization reaction: pH 7.0.

Based on the association/dissociation curve obtained by the above-mentioned measurement, an RU value obtained by subtracting the RU value measured before binding from the RU value measured after binding can be used as a value representing the binding level (per 1 mm$^2$) between acid-denatured human IgG, which is an analyte, and the peptide tag, which is a ligand; that is, a value representing the ability of the peptide tag to bind to the acid-denatured human IgG.

Dissociation constant (Kd), affinity constant (Ka), association rate constant (ka), and dissociation rate constant (kd), which indicate the binding state between the peptide tag of the present invention and acid-denatured human IgG, are particularly preferably determined by surface plasmon resonance spectrum analysis according to the above-mentioned conditions. According to this analysis, dissociation constant (Kd) for the binding between the peptide tag of the present invention and acid-denatured human IgG (e.g., acid-denatured human IgG in polyclonal human IgG (Sigma)) preferably ranges from 0.1 nM to 50 nM and from 10 nM to 50 nM, for example. This indicates that the binding force of the peptide tag of the present invention for binding to acid-denatured human IgG is much stronger than that of numerous conventional IgG-binding peptides. Meanwhile, dissociation rate constant (kd) for the binding between the peptide tag of the present invention and acid-denatured human IgG preferably ranges from $10^{-3}$ sec$^{-1}$ to $10^{-5}$ sec$^{-1}$. Such dissociation rate constant (kd) values are almost equivalent to general dissociation rate constant ($10^{-4}$ to $10^{-6}$ sec$^{-1}$) values of human IgG, suggesting that the peptide tag of the present invention can sufficiently retain its binding to acid-denatured human IgG.

The peptide tag of the present invention and human IgG, and particularly, acid-denatured human IgG, exhibit the above-mentioned binding under non-reducing conditions. In the present invention, the term "under non-reducing conditions" refers to redox state such that cleavage of disulfide bonds is not induced. More specifically, the term "under non-reducing conditions" refers to, for example, conditions such that a reducing agent (e.g., DTT) that causes cleavage of disulfide bonds is not contained in an amount sufficient for inducing such cleavage in the reaction system.

In the present invention, with the use of a high level of binding of the peptide tag of the present invention to acid-denatured human IgG as described above, human IgG or an Fc region-containing fragment thereof in a sample can be successfully detected. The peptide tag of the present invention can stably retain the binding with acid-denatured human IgG Fc region, enabling detection with high sensitivity.

The present invention also relates to a method for detecting human IgG or an Fc region-containing fragment thereof in a sample, comprising the following steps a) to c):

a) acid treating a sample;

b) contacting the peptide tag of the present invention with the acid-treated sample, and c) measuring the level of binding produced in step b) between the peptide tag and human IgG or an Fc region-containing fragment thereof.

This detection method of the present invention can be applied to any sample that contains or may contain human IgG or a Fc region-containing fragment of human IgG. Examples of appropriate samples include, but are not limited to, biological samples such as blood, body fluids (e.g., saliva, semen, tears, digestive juice, and ascites), tissues, tissue fluids, cells, cell extracts, and cultures. Such a biological sample may also be a clinical trial specimen. Other examples of appropriate samples include a culture supernatant of a human monoclonal IgG-producing hybridoma and a sample for immunoassay. A sample is preferably contacted in an acid-denatured form with the peptide tag. Hence, before contacting with the peptide tag, IgG or the like in a sample is acid-denatured by acid treatment as described above. The pH of an acid-treated sample is preferably neutralized before contacting with the peptide tag. Alternatively, a sample may be prepared or collected originally under acidic conditions. For such sample, the step of acid treatment may be omitted and the sample can also be used as an "acid-treated sample." Also, a sample is preferably contacted in a state of being prepared in the form of liquid (e.g., a solution or a suspension) with the peptide tag of the present invention.

To contact the peptide tag of the present invention with a sample, for example; an acid-treated sample is added to the peptide tag of the present invention, or vice versa. Contacting of the peptide tag of the present invention with an acid-treated sample is preferably carried out under non-reducing conditions. Depending on a technique employed for detection of binding, unbound substances are preferably removed from the peptide tag of the present invention by washing, fractionation, or the like after contacting the peptide tag of the present invention with the sample. When human IgG or an Fc region-containing fragment thereof is present in a sample, at least some of human IgGs or Fc region-containing fragments thereof in the sample becomes acid-denatured form via acid treatment of the sample, and the subsequent contact of the peptide tag of the present invention with the sample results in that the acid-denatured IgG or the Fc fragment thereof and the peptide tag of the present invention are bound with high efficiency. Here, the expression "binding produced in step a) between the peptide tag and human IgG or an Fc region-containing fragment thereof" refers to a state such that a significant level of the peptide tag binds mainly to acid-denatured human IgG or an Fc region-containing fragment thereof as a result of contacting of the peptide tag of the present invention with the acid-treated sample.

Binding between the peptide tag and human IgG or an Fc region-containing fragment thereof can be measured by any method for measuring molecular interactions, which is well-known to persons skilled in the art. Examples of such measurement methods include, but are not limited to, immunoprecipitation, gel shift assay, ELISA, surface plasmon resonance analysis, Quartz Crystal Microbalance (QCM) (written by Masahiro Seo, "Quartz Crystal Microbalance method," Surface Finishing, Vol. 45—No. 10, (1994) p. 1003-1008, and U.S. Pat. No. 5,869,763), Fluorescence Correlation Spectroscopy (FCS), Fluorescence Intensity Multiple Distribution analysis (FIMDA), and Fluorescence Cross-Correlation Spectroscopy (FxCS). These methods are well-known to persons skilled in the art and many measuring instruments and reagents for measurement are marketed corresponding to each of these methods. In the present invention, it is particularly preferred to measure the binding level with the use of surface plasmon resonance analysis, for example, in terms of that human IgG binding to the peptide tag can be separated and purified after the detection. The above measurement of the binding level may be carried out simultaneously or successively with the step of contacting the peptide tag of the present invention with an acid-treated sample.

When the binding is confirmed as a result of measurement, this indicates successful detection of the presence of human IgG or an Fc region-containing fragment thereof contained in a sample.

Successful detection is possible according to this method, even if human IgG or an Fc region-containing fragment thereof is present alone in a sample or if the same is present in a state of binding to another substance such as a labeling substance. According to the method of the present invention, human IgG or the like that is fused to the terminus of any protein, human IgG or the like displayed by a phage vector, human IgG or the like immobilized on a solid-phase support can also be detected. In the present invention, detection of such human IgG or such Fc region-containing fragment thereof in a state of binding to another substance is also included in the examples of "detection of human IgG or an Fc region-containing fragment thereof."

This method can also be appropriately used for detection of particularly a human Fc fusion protein (a fusion protein of a human Fc fragment and any protein) that is often used in biochemical and molecular biological fields, such as a fusion protein of an extracellular domain of a TNF receptor and a human Fc fragment.

According to the present invention, human IgG or an Fc region-containing fragment thereof in a sample can be successfully separated or purified based on the high level of binding of the peptide tag of the present invention to acid-denatured human IgG. The peptide tag of the present invention can stably retain the binding with acid-denatured human IgG Fc region, so as to enable separation or purification with high recovery efficiency.

For example, the present invention also relates to a method for purifying human IgG or an Fc region-containing fragment thereof in a sample, comprising the following steps a) and b):

a) contacting the peptide tag of the present invention with an acid-treated sample, thereby binding human IgG or an Fc region-containing fragment thereof in a sample to the peptide tag; and b) separating the human IgG or the Fc region-containing fragment thereof bound to the peptide tag prepared by step a) from the sample.

The IgG separation or purification method of the present invention can be applied to any sample, as long as it contains or may contain human IgG or a Fc region-containing fragment of human IgG. Samples to be used herein are as described for the above detection method. Similarly, a sample is preferably contacted in an acid-denatured state with the peptide tag. Accordingly, prior to contacting with the peptide tag, a sample is acid-denatured via the above-described acid treatment. Alternatively, a sample may be prepared or collected originally under acidic conditions. Such a sample can also be used as an "acid-treated sample." The pH of such an acid-treated sample is preferably neutralized prior to contacting of the sample with the peptide tag.

To contact the peptide tag of the present invention with a sample, for example; the acid-treated sample is added to the peptide tag of the present invention, or vice versa. Contacting of the peptide tag of the present invention with an acid-treated sample is preferably carried out under non-reducing conditions. Through contacting of the peptide tag of the present invention with a sample treated with acid, at least some of human IgGs or Fc region-containing fragments thereof in the sample becomes acid-denatured form and then the acid-denatured human IgG or a Fc region-containing fragment thereof and the peptide tag of the present invention are bound.

After contacting of the peptide tag of the present invention with an acid-treated sample, human IgG or an Fc region-containing fragment thereof bound to the peptide tag as a result of contacting can be separated from the sample by a technique for separation and purification of biological molecules well-known to persons skilled in the art. For example, when the peptide tag immobilized on a solid-phase support such as a column, a plate, or a sensor chip is used, human IgG or an Fc region-containing fragment thereof bound to the peptide tag on the solid-phase support can be separated from the other ingredients in the sample by washing the solid-phase support after contacting under conditions where the peptide tag does not dissociate from the solid-phase support. Alternatively, when the peptide tag immobilized on a solid-phase support such as a magnetic bead is used, human IgG or an Fc region-containing fragment thereof bound to the peptide tag on the magnetic beads can be separated from the other ingredients in the sample by removing magnetic beads or the like with the use of magnet or the like from the sample after contacting and then preferably washing them. Such separation step can be carried out simultaneously (or in parallel) or successively with the step of contacting the peptide tag of the present invention with a sample. For example, when surface plasmon resonance analysis or chromatography is employed in the method of the present invention, at the same time that human IgG or the like in an applied sample solution contacts with and binds to the immobilized peptide tag so as to be retained thereby, the other ingredients in the sample solution flow out without being bound to the peptide tag and are thus separated from human IgG or the like bound to the peptide tag.

The presence of human IgG or an Fc region-containing fragment thereof, which has been bound to the peptide tag and then separated from a sample, can also be confirmed by Western blotting or the like.

If necessary, human IgG or an Fc region-containing fragment thereof can be further dissociated and isolated from such a separated conjugate of the peptide tag and the acid-denatured human IgG or the Fc region-containing fragment thereof. Human IgG or an Fc region-containing fragment thereof can be dissociated from the peptide tag by, but not limited thereto, placing it under acidic conditions, for example. Such acidic conditions can be easily adjusted by persons skilled in the art. For example, an acidic solution such as glycine-hydrochloric acid (pH 2.1) is added to human IgG or an Fc region-containing fragment thereof bound to the peptide tag. The human IgG or Fc region-containing fragment thereof may also be separated by dialysis from the peptide tag. Human IgG or an Fc region-containing fragment thereof that becomes free from the peptide tag may further be purified using a protein purification method well-known to persons skilled in the art, such as various chromatography methods and immunoprecipitation.

Human IgG or an Fc region-containing fragment thereof, which may be present alone in a sample, or bound to another substance such as a labeling substance, can be appropriately separated or purified by the present method. According to the method of the present invention, human IgG or the like fused to the terminus of any protein, human IgG or the like displayed by a phage vector, human IgG or the like immobilized on a solid-phase support such as magnetic beads can be separated or purified. The method of the present invention is appropriately employed for separation or purification of, particularly, a human Fc fusion protein (i.e., a fusion protein of a human Fc fragment and any protein), which is often used in biochemical and molecular biological fields, for example, a fusion protein of an extracellular domain of a TNF receptor and a human Fc fragment. In the present invention, such purification of human IgG or an Fc region-containing fragment thereof, which is bound to another substance, is also included in "purification of human IgG or an Fc region-containing fragment thereof"

Moreover, in the present invention, acid-denatured human IgG or an Fc region-containing fragment thereof, which is originally present in a sample, can be captured and separated (removed) from the sample with the use of a high level of the binding of the peptide tag of the present invention to acid-denatured human IgG or the acid-denatured Fc region thereof. The use of this method makes it possible to, for example, remove contaminating acid-denatured human IgG or an Fc region-containing fragment thereof from the sample containing human IgG to purify human IgG homogenously with high purity.

Therefore, the present invention also relates to, for example, a method for removing acid-denatured human IgG or an Fc region-containing fragment thereof from a sample, comprising the following steps a) and b):

a) contacting the peptide tag of the present invention with a sample; and b) removing human IgG or an Fc region-containing fragment thereof bound to the peptide tag prepared by step a) from the sample.

Also, the present invention also relates to, for example, a method for purifying human IgG or an Fc region-containing fragment thereof comprising the following steps a) to c):

a) contacting the peptide tag of the present invention with a sample containing human IgG or an Fc region-containing fragment thereof, thereby binding acid-denatured human IgG or an Fc region-containing fragment thereof in the sample to the peptide tag;

b) separating the acid-denatured human IgG or Fc region-containing fragment thereof bound to the peptide tag prepared by step a) from the sample; and c) collecting the remaining sample after separation above.

Such method for removing acid-denatured human IgG or the like (i.e., purification method of human IgG or the like) can overcome various problems concerning conventional human IgG purification techniques. For example, for purification of a human antibody using a Protein A column in the production of an antibody such as an antibody drug, an antibody is generally eluted from the column using an acidic solution (typically at pH 2.1 to 2.7). However, this method is problematic in that some antibodies are denatured mainly due to acid treatment upon elution, so as to lower the quality of the thus obtained antibody product. Removal of such denatured antibodies generally further requires relatively complicated procedures such as ion exchange or gel filtration. However, by the use of the peptide tag of the present invention, for example, by the use of an affinity column on which the peptide tag of the present invention is immobilized, an acid-denatured IgG antibody can be efficiently removed by a single-step procedure. Purification of a human antibody using a Protein A column is also problematic in that when an antibody is eluted from a column using an acidic solution (typically, at pH 2.1 to 2.7), the yield significantly decrease (60% to 80%). This may be because antibodies denatured and undergone conformational changes by acid treatment tend to aggregate and such an aggregate form of antibodies binds to a resin so as to be eluted with difficulty. In the present invention, to avoid such decrease in the recovery rate of human IgG, for example, PEG or saccharide with high solubility can be attached to the peptide tag of the present invention and the resultant can be added to an acidic eluting solution for use, thereby allowing an acid-denatured antibody and the peptide tag of the present invention attached to PEG or saccharide to be bound rapidly in a column, so that the antibody can be recovered without its adsorption to the column resin. From the thus recovered antibody, the peptide tag of the present invention bound thereto can also be removed by dialysis or the like.

3. Other Embodiments

Purification of Protein Using the Property of Binding of Peptide Tag to IgG

With the use of the high level of binding of the peptide tag of the present invention to acid-denatured human IgG, a protein to which the peptide tag is attached (ligated) can be specifically separated. The present invention also provides, with the use of this finding, a separation/purification method by attaching the peptide tag according to the present invention to a protein of interest and then separating and purifying the protein using acid-treated human IgG or an Fc region-containing fragment thereof.

For example, the present invention relates to a method for purifying a protein, comprising the following steps a) to c):

a) producing a fusion protein containing a protein linked to the peptide tag of the present invention and then preparing a sample containing the fusion protein;

b) contacting the sample prepared by step a) with acid-treated human IgG or an Fc region-containing fragment thereof, thereby binding the fusion protein to the human IgG or Fc region-containing fragment thereof; and c) separating the fusion protein bound to the human IgG or Fc region-containing fragment thereof prepared by step b) from the sample.

The above-mentioned term "fusion protein" refers to a protein in which the peptide tag of the present invention is attached (ligated) to a protein, preferably at the N-terminus or the C-terminus. Such fusion protein may have a linker containing a cleavable link (e.g., protease recognition site) between the peptide tag and a protein of interest.

A fusion protein can be produced by ligating the peptide tag of the present invention to preferably the N-terminus or the C-terminus of any protein to be separated and purified, according to e.g., a recombinant method. More specifically, for example, a recombinant expression vector may be constructed by inserting in-frame a DNA fragment encoding a protein of interest to the 5' side or the 3' side of DNA encoding the peptide tag of the present invention incorporated in a vector, introduced into host cells to prepare a transformant, cultured under conditions enabling the expression (e.g., in the presence of an expression-inducing substance), and then the thus produced fusion protein can be recovered from the culture or cultured cells. Thus, a single polypeptide comprising the peptide tag and the portion of the protein of interest can be obtained as a fusion protein.

In the method of the present invention, preferably, first such a fusion protein is prepared and then a sample containing the fusion protein is prepared. A sample is, but is not limited to, preferably a liquid preparation such as a solution or a suspension, for example.

In the meantime, human IgG or an Fc region-containing fragment thereof is more preferably used in a form immobilized on a solid-phase support such as a bead, a column, or a plate. Human IgG or an Fc region-containing fragment thereof is preferably subjected to acid treatment prior to contacting it with a sample. Acid treatment may be carried out as described above. For example, acid treatment can be carried out by adjusting the pH of a solution containing human IgG or an Fc region-containing fragment thereof at pH 1.5 to 2.7 and then performing treatment for at least 5 minutes. Through such acid treatment, human IgG or an Fc region-containing fragment thereof is altered to be an acid-denatured form thereof, so that the capturing efficiency of the fusion protein having the peptide tag of the present invention can be significantly improved. The pH of an acid-treated sample is preferably neutralized prior to contacting it with a fusion protein having the peptide tag. When such acid-treated human IgG or an Fc region-containing fragment thereof is contacted with the above-prepared sample containing a fusion protein, the fusion protein in the sample binds to the acid-denatured human IgG or Fc region-containing fragment thereof via the peptide tag.

In this method, the fusion protein that has been bound to the human IgG or Fc region-containing fragment thereof in such a manner is preferably further separated from the sample.

The above-described step of contacting a sample with acid-treated human IgG or an Fc region-containing fragment thereof and the step of separating a fusion protein from a sample may be basically carried out in a manner similar to the detection or purification method of the present invention as described above.

Moreover, when a fusion protein has a linker containing a cleavable link (e.g., protease recognition site), the fusion protein is separated from the sample and then subjected to cleavage such as protease treatment so as to separate a protein of interest from the peptide tag of the present invention. and they can be each recovered and purified separately.

According to the protein purification method of the present invention, a protein of interest can be conveniently and specifically separated and purified with high trapping efficiency.

Kit

The present invention also provides a kit for detecting or purifying human IgG or an Fc region-containing fragment of human IgG, which comprises at least one of: the peptide tag of the present invention; a recombinant bacteriophage displaying the peptide tag; a fusion protein containing a protein linked to the peptide tag; a solid-phase support on which the peptide tag is immobilized; a vector comprising DNA encoding the peptide tag; and a transformant comprising the vector. The kit can be appropriately used for providing the peptide tag of the present invention in the above method of the present invention for detecting or purifying human IgG or the like.

Furthermore, the present invention provides a kit for producing a purification tag-fused protein that can be easily purified using the property of binding to acid-denatured human IgG, which comprises at least one of a DNA encoding the peptide tag of the present invention; a vector (particularly, an expression vector) comprising a DNA encoding the peptide tag of the present invention; and a transformant comprising the vector. The term "purification tag" refers to an additional peptide sequence that facilitates affinity purification of a protein, such as His tag or GST tag. The term "purification tag-fused protein" refers herein particularly to a fusion protein in which the peptide tag of the present invention is attached (ligated).

With the use of this kit, an expression vector comprising a DNA fragment prepared by ligating in-frame a DNA encoding a protein of interest to a DNA encoding the peptide tag of the present invention can be constructed and then placed under expression conditions (for example, host cells can be transformed with the expression vector and then the thus obtained transformant can be cultured in the presence of an expression-inducing substance), and therefore a fusion protein in which the peptide tag of the present invention is ligated can be produced.

EXAMPLES

The present invention will be explained more specifically with reference to the following examples. However, the technical scope of the present invention is not limited to these examples.

In addition, polyclonal human IgG antibodies, polyclonal human antibodies IgG1, IgG2, IgG3, and IgG4, polyclonal human IgA antibodies, polyclonal human IgE antibodies, and polyclonal mouse antibodies IgG, IgA, and IgE used in the following Examples were purchased from Sigma. Moreover, disulfide (S—S) bond formation between cysteine residues of the peptide was carried out by air oxidation in a buffer (pH 8) and then confirmed by reverse phase HPLC and MALDI-TOF mass spectrometry.

Example 1

Seeking Human Antibody-Binding Motif

1) Construction of T7 Phage Random Peptide Library

Libraries displaying random peptides, C-$(X)_{8-10}$-C (SEQ ID NO: 24) or $(X)_3$-C-$(X)_{8-10}$-C-$(X)_3$ (SEQ ID NO: 25), exerting 8 amino acid sequence patterns on T7 phages were each constructed according to T7Select$^{(R)}$ System Manual (Novagen) using T7Select10-3b vector (Novagen). For details concerning construction of T7 phage random peptide libraries, see Krumpe L R, et al., Proteomics, (2006) 6 (15): p. 4210-4222 and T7Select$^{(R)}$ System Manual (Novagen). In addition, C-$(X)_{8-10}$-C (SEQ ID NO: 24) denotes a peptide sequence in which 8 to 10 consecutive any amino acid residues (X) are sandwiched between cysteine residues (Cys) on the N-terminus and on the C-terminus. Also, $(X)_3$-C-$(X)_{8-10}$-C-$(X)_3$ (SEQ ID NO: 25) denotes a peptide sequence in which, from the N-terminus to the C-terminus, 3 consecutive any amino acid residues, a cysteine residue (Cys), 8 to 10 consecutive any amino acid residues, a cysteine residue, and 3 consecutive any amino acid residues are linked.

Briefly, a population of DNA fragments encoding the above random peptides was cloned into T7Select10-3b vectors using T7Select Cloning Kit (Novagen). The vectors were then packaged into phages and propagated, thereby constructing a library. In the thus constructed libraries, the above peptides were displayed on the surface of the phages through the expression of the peptides, which were each fused to the C-terminus of T7 10B capsid protein (approximately 348 amino acids).

2) Biopanning for Human IgG

Each well of 96-well microplate (Nunc, Maxisorp) was coated with human IgG (500 ng/100 µl/well; serum-derived polyclonal antibody; hereinafter the same is used) and then 0.5% BSA was added for blocking. The phage library (5.0× $10^{10}$ pfu), which was constructed in the section 1) above, in PBS with 0.5% BSA was added to the well, followed by 1 hour of reaction at room temperature. Wells after reaction were washed with PBS/0.1% Tween20 (PBST), and then Escherichia coli BLT5615 was added. The Escherichia coli BLT5615 cells were recovered after infection with phages, and then cultured for the propagation of phages. The phages were collected with 10% (W/V) PEG from supernatants after culturing and then used for the next panning. The biopanning process was repeated 5 rounds in total, so that phages specifically binding to human IgG were enriched. In the step of washing wells, washing was repeated 5 times in the $1^{st}$ to $3^{rd}$ rounds and 10 times in the $4^{th}$ and $5^{th}$ rounds. The concentration of a surfactant, Tween20, contained in a washing solution was 0.1% in the $1^{st}$ and $2^{nd}$ rounds, but increased to 0.3% in the $3^{rd}$ and $4^{th}$ rounds and 0.5% in the $5^{th}$ round. After 5 rounds of biopanning, Escherichia coli BLT5615 cells were plated and then phages were added onto for infection, so that phage plaques were formed and the phages were cloned.

3) ELISA Assay

Each well of 96-well microplate (Nunc, Maxisorp) was coated with human IgG (100 ng/50 µl/well) in 0.1M $NaHCO_3$ solution and then 0.5% BSA in PBS was added for blocking. As a control protein, BSA (bovine serum albumin) in PBS was used, instead of human IgG. After blocking, a population of T7 phages (5×$10^{10}$ pfu/well) obtained in each round of the section 2) above was added to each well, followed by 1 hour of reaction and then 3 times of washing with PBS/0.1% Tween20 (PBST). A biotinylated mouse anti-T7 phage antibody (Novagen) was added to each well after washing and then HRP-labeled streptavidin (SA-HRP) (Jackson Immuno Research) was added. Furthermore, T7 phages binding to human IgG on wells were detected based on color reaction using a TMB solution (Wako Chemicals). Detection was carried out by measuring absorbance at 450 nm using an ELISA plate reader (ImmunoMini NJ-2300, InterMed, Tokyo, Japan).

The course of enrichment of phages that bind to human IgG in each round, as determined by the ELISA assay, is shown in FIG. 1. As shown in FIG. 1, in the library of C-$(X)_{8-10}$-C type, human IgG-binding phages were significantly enriched in the 4$^{th}$ round. On the other hand, in the library of (X)$_3$-C-(X)$_{8-10}$-C-(X)$_3$ type, no effective enrichment of human IgG-binding phages was observed (FIG. 1). In both libraries, no sufficient enrichment of BSA-binding phages was observed.

Next, individual phage clones cloned from a mixed population of the C-(X)$_{8-10}$-C (SEQ ID NO: 24) type after the 5$^{th}$ round were evaluated for their binding activity to human IgG by an ELISA assay as described above. As a result, binding activity specifically to human IgG was observed in 25 clones out of 40 clones. Hence, to determine the amino acid sequences of peptides displayed by phage clones confirmed to exhibit the binding activity, peptide-encoding DNAs ligated to the 3' side of G10 capsid protein gene within phage DNA were subjected to sequencing using an ABI DNA sequencer 373A-36S. As primers for sequencing reaction, an upstream primer: 5'-GGAGCTGTCGTATTCCAGTC-3' (SEQ ID NO: 13) and a downstream primer: 5'-AACCCCT-CAAGACCCGTTTA-3' (SEQ ID NO: 14) were used. As a result of sequencing, the amino acid sequences of peptides displayed by phage clones confirmed to exhibit the binding activity to human IgG were classified into 6 types (hG-1 to hG-6 peptides) in Table 1 below. These 6 types of peptides were believed to specifically bind to human IgG. Moreover, it was shown that these 6 types of peptide sequences contain either or both of two common motifs consisting of 3-amino acid sequences, GYW and WGL, between the N-terminal cysteine residue and the C-terminal cysteine residue. In Table 1, each peptide sequence is described using one letter codes for amino acids.

TABLE 1

| Peptide | Amino acid sequence | SEQ ID NO: |
|---|---|---|
| hG-1 | C GYWRSEWGL C | 1 |
| hG-2 | CT GFWEREWGL C | 2 |
| hG-3 | C LYWPRLWGL C | 3 |
| hG-4 | CT GYWPKAWGL C | 4 |
| hG-5 | C YWAVRWGLLGC | 5 |
| hG-6 | C GYWADVWQIH C | 6 |
| High-consensus residue | C YW WGL C | |

Example 2

Evaluation of Binding Specificity to Human IgG

1) Evaluation of ELISA Assay

Of phage clones isolated in Example 1, representative phage clones G-1 to G-6 displaying peptides hG-1 to hG-6, respectively, were subjected to an ELISA assay as described in Example 1 to evaluate the binding specificity to human IgG (hIgG). As control proteins, human IgA (hIgA), IgE (hIgE), and IgM (hIgM), mouse IgG (mIgG), IgA (mIgA), and IgE (mIgE), human transferrin (hTF), human serum albumin (HSA), bovine serum albumin (BSA), and gelatin were used. The results are shown in FIG. 2.

Figure 2:
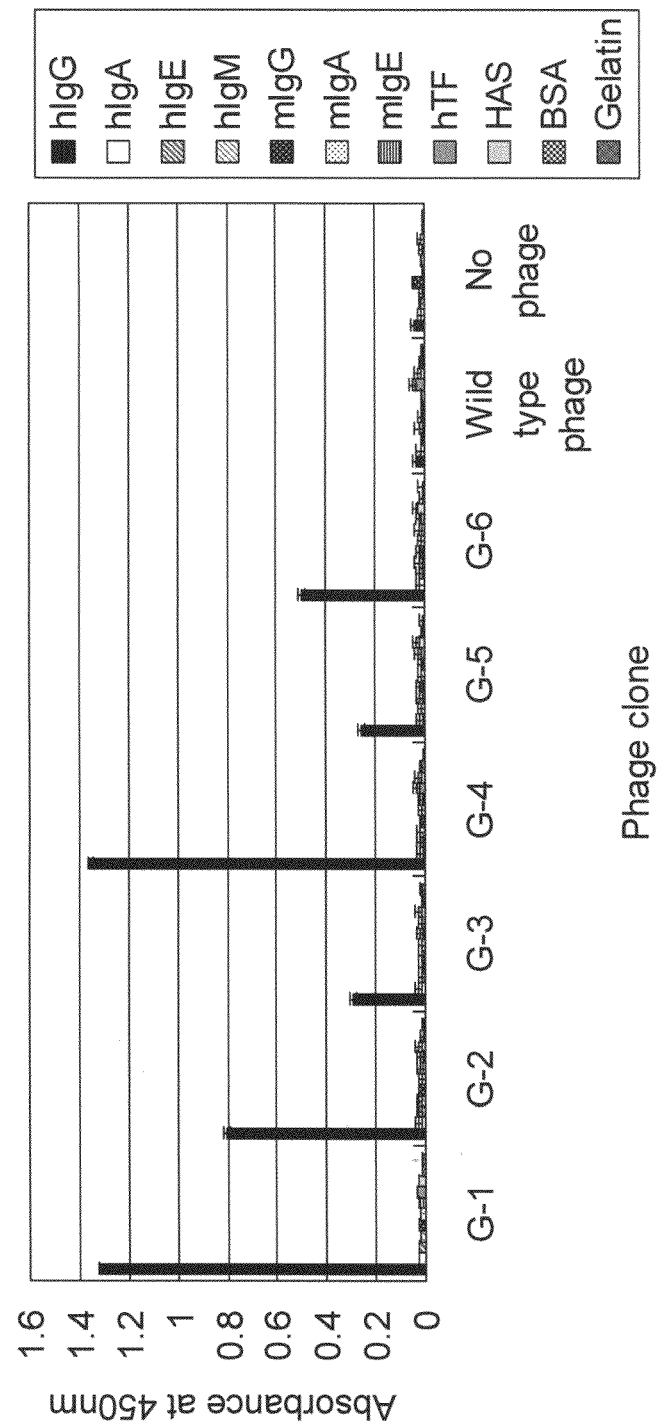
FIG. 2 shows the human IgG-binding specificity of the obtained IgG-specific phage clones. The bars indicate, from the left, per each phage, the property of binding to hIgG, hIgE, hIgA, hIgE, hIgM, mIgG, mIgA, mIgE, hTF, HSA, BSA, and gelatin, respectively.

All the phage clones G-1 to G-6 exhibited extremely high binding specificities to human IgG, although they vary somewhat in the intensities (closed (black) bar in FIG. 2), but exhibited almost no binding activity to other control proteins including human IgA, IgE, and IgM, mouse IgG, IgA, and IgE, ThF, HSA, BSA, and gelatin. Therefore, it was shown that the peptides hG-1 to hG-6 displayed by the phage clones G-1 to G-6 specifically bind to human IgG, but does not substantially bind to antibodies of other classes, antibodies of other biological species, or other proteins.

Figure 3:
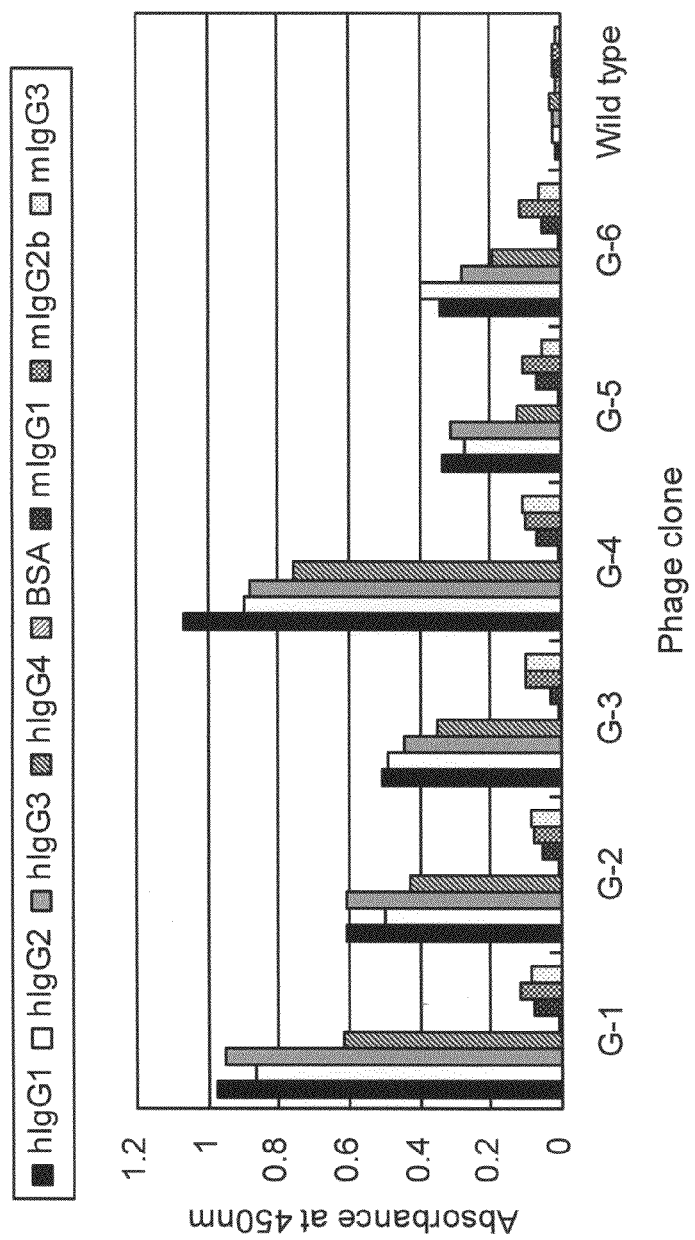
FIG. 3 shows the binding activity of the obtained IgG-specific phage clones to human IgG isotypes (IgG1, IgG2, IgG3, and IgG4). The bars indicate, from the left, per each phage, the property of binding to hIgG1, hIgG2, hIgG3, hIgG4, BSA, mIgG1, mIgG2b, and mIgG3, respectively.

Furthermore, the binding activity of phage clones G-1 to G-6 to human IgG isotypes (subclasses) hIgG1 to hIgG4 was confirmed by an ELISA assay as described above. As control proteins, mouse IgG isotypes IgG1, IgG2b, and IgG3, and BSA were used. The results are shown in FIG. 3. As shown in FIG. 3, the phage clones G-1 to G-6 strongly bound to all of these human IgG isotypes. On the other hand, G-1 to G-6 exhibited no significant binding activity to all the mouse IgG isotypes as well as, of course, BSA.

2) Evaluation by Surface Plasmon Resonance Analysis

The phage clones G-1, G-2, and G-4 confirmed to have stronger binding activity were subjected to surface plasmon resonance (SPR) analysis. SPR analysis was carried out using BIAcore2000 (BIAcore) at 25° C. Necessary reagents and sensor chips were purchased from BIAcore and then used. Human IgG (ligand) was immobilized on a sensor chip CM5 according to amine coupling protocols as recommended by the manufacturer. As a control, a sensor chip CM5 on which human IgA or IgE had been immobilized was also prepared. Immobilization reaction was carried out under the condition of pH 5 and the amount of such a ligand to be immobilized was adjusted so that RU (response unit) ranged from 1500 to 2000. Next, T7 phage clone G-1, G-2, or G-4 (analyte) purified by ultracentrifugation was injected at a flow rate of 10 μl/min through a flow cell with a sensor chip ($1.0 \times 10^{11}$ pfu/ml) on which human IgG had been immobilized and then binding reaction with human IgG was measured. Subsequently, dissociation reaction was measured via washing with running buffer (HBS-T; buffer composition: 10 mM HEPES, 0.15 M NaCl, 3.4 mM EDTA, 0.005% Tween 20 (pH 7.4)). 0.2 M glycine-HCl buffer (pH 2.7) was used for washing/elution of the bound analytes from the sensor chips. Binding parameters were analyzed using BIA evaluation Version 3.2 software.

As a result, all the clones G-1, G-2, and G-4 exhibited specific binding to human IgG immobilized on sensor chips, but did not bind to immobilized human IgA and IgE. The results are consistent well with the results of evaluating the binding specificity by the above ELISA assay.

Example 3

Prediction of Binding Site in hIgG

To identify the binding sites in human IgG for the phage clones G-1 to G-6, a competitive ELISA assay was conducted with Protein A (SpA; cell wall constituent protein derived from *Staphylococcus aureus*) known to specifically bind to IgG Fc fragment. The ELISA assay was conducted basically in a manner similar to that in Example 1. Specifically, wells coated with human IgG (100 ng/50 μl/well) were blocked with 0.5% BSA. T7 phage clones G-1 to G-6 ($5 \times 10^{10}$ pfu/well) and SpA with various concentrations were added simultaneously to the wells, incubation was carried out at room temperature for 1 hour, and then detection was carried out.

Concentrations of SpA added herein were 0 ng/well, 15 ng/well, 30 ng/well, 60 ng/well, 125 ng/well, 250 ng/well, and 500 ng/well.

Figure 4:
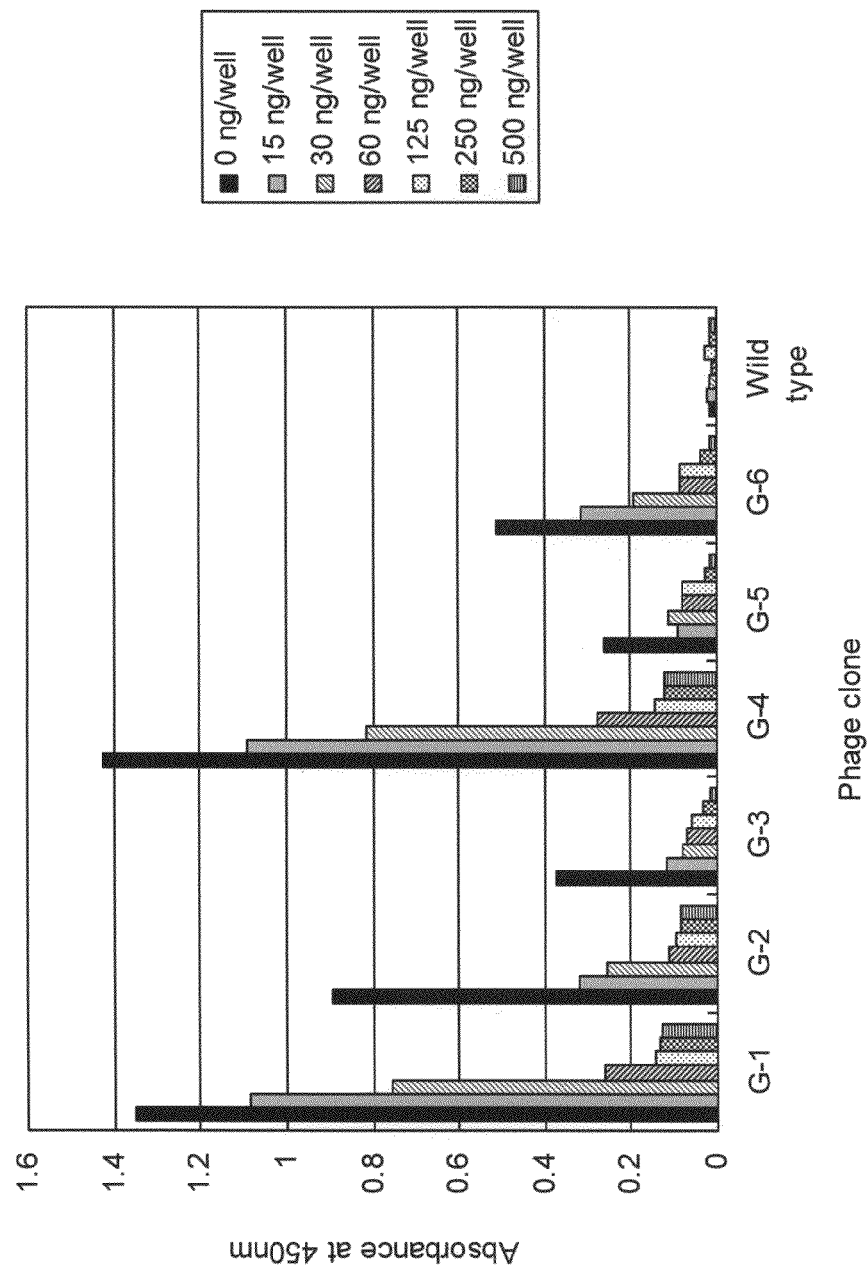
FIG. 4 shows the inhibition with Protein A against the binding of the obtained IgG-specific phage clones to human IgG. The bars indicate, from the left, per each phage, the property of binding to human IgG when 0 ng/well, 15 ng/well, 30 ng/well, 60 ng/well, 125 ng/well, 250 ng/well, and 500 ng/well of Protein A (SpA) were each added, respectively.

The results are shown in FIG. 4. As shown in FIG. 4, the higher the concentration of SpA added, the more strongly inhibited binding of G-1 to G-6 to human IgG antibody. The results showed that the T7 phage clones G-1 to G-6 recognize and bind to the site same as or a site in the vicinity of the SpA binding site within IgG. Since SpA is known to bind to the junction of CH2 domain and CH3 domain of human IgG Fc, it was considered that T7 phage clones G-1 to G-6 also bind to a site around the junction.

Example 4

Evaluation of Disulfide Bond

To evaluate the significance of intramolecular disulfide bond to the binding activity to human IgG of the peptide displayed by the phage clones obtained in the Examples above, the binding activity of T7 phage clones to hIgG was evaluated by ELISA in the presence of dithiothreitol (DTT) (under reductive condition) and in the presence of oxidized glutathione (GSSG) (under oxidative conditions). The ELISA assay was basically carried out in a manner similar to that in Example 1. Specifically, wells coated with human IgG (100 ng/50 µl/well) were blocked with 0.5% BSA and then the reaction product obtained in advance via 1 hour of reaction between GSSG or DTT (50, 30, or 10 mM) and T7 phage clone G-1 was added to the wells. After 1 hour of incubation at room temperature, detection was carried out. The results are shown in FIG. 5.

Figure 5:
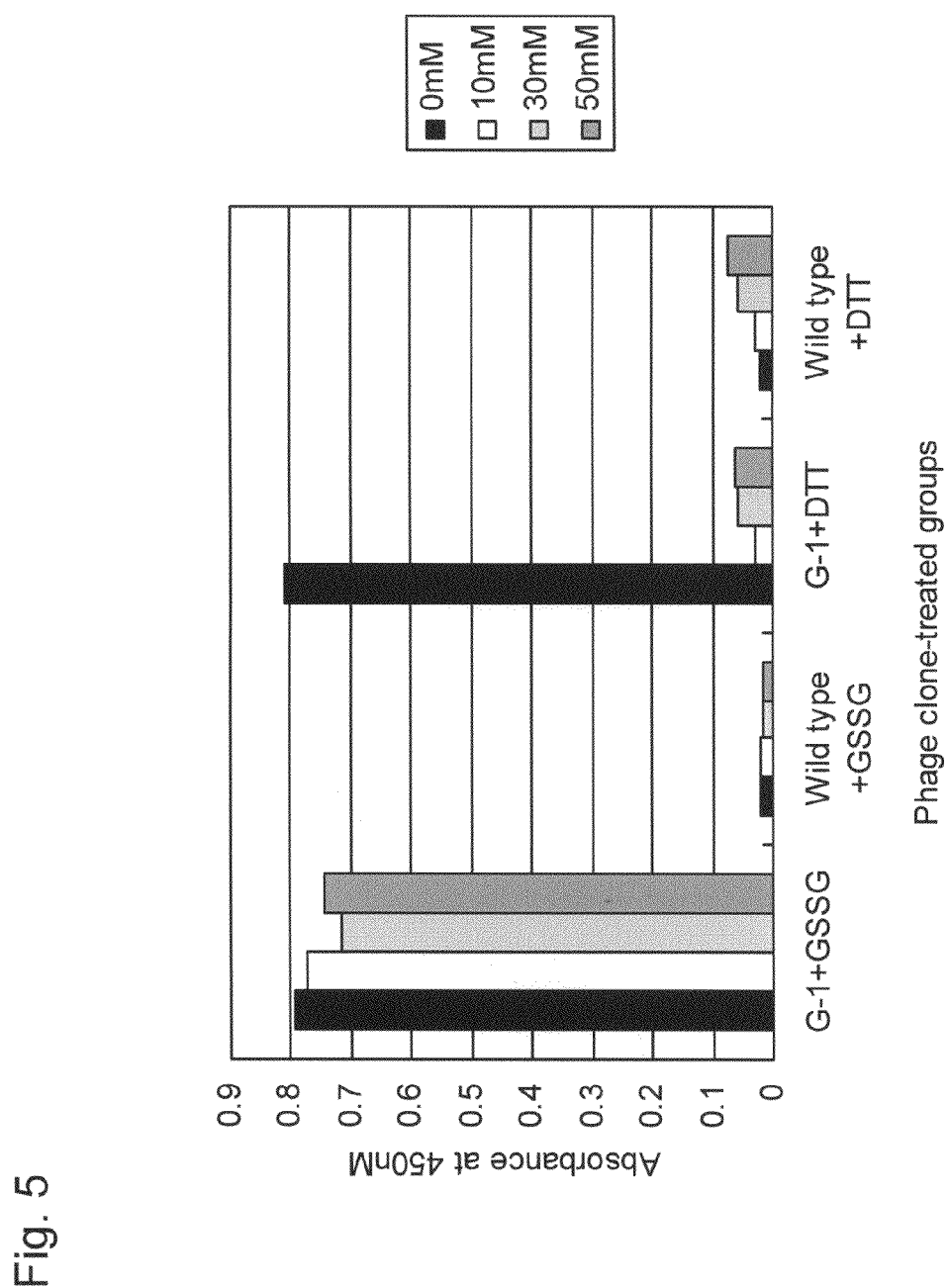
FIG. 5 shows the binding activity of the IgG-specific phage clones to human IgG under reducing conditions and oxidizing conditions. The bars indicate, from the left, per each experimental group, the property of binding of a phage to human IgG when 0 mM (no addition), 30 mM, and 50 mM GSSG or DTT were each added, respectively.

As shown in FIG. 5, under reductive conditions, in which disulfide bonds were cleaved, while G-1 almost completely lost its binding activity to human IgG at a DTT concentration of 10 mM or higher. However, under oxidative conditions, in which disulfide bonds were formed, no changes were observed in the binding activity of G-1 to human IgG at any concentration of GSSG. In addition, under these conditions, no changes were observed in the infectivity of the phage to *Escherichia coli*. Therefore, it was considered that a decrease in the binding activity of phage clone G-1 to IgG under reducing conditions was not due to disruption or the like of phage particles, but due to the cleavage of intramolecular disulfide bond (S—S bond) in peptide hG-1 displayed by G-1.

The above results revealed that intramolecular disulfide bond (S—S bond) formation between the cysteine residues in the peptides displayed by the phage clones obtained in the Examples above plays an important role in the binding activity to human IgG.

Example 5

Binding Activity of Synthetic Peptide to Human IgG

Based on the amino acid sequences of peptides displayed by the phage clones G-1 and G-4 confirmed to exhibit particularly high binding activity to IgG in the above Examples, synthetic peptides were designed and synthesized and then biotinylated by a conventional method. Biotinylated IMGpep-1 (biotin-spacer-GCGYWRSEWGLCG (SEQ ID NO: 7)) and biotinylated IMGpep-4 (biotin-spacer-GCTGYWPKAWGLCG (SEQ ID NO: 9) were prepared. Further, biotinylated IMGpep-1E6Q (biotin-spacer-GCGYWRSQWGLCG (SEQ ID NO: 10)) was prepared, in which "E (Glu)" located between common motifs GYW and WGL in the IMGpep-1 sequence was substituted with "Q (Gln)." Furthermore, biotinylated IMGpep-4K6R (biotin-spacer-GCTGYWPRAWGLCG (SEQ ID NO: 11)) was prepared, in which "K(Lys)" located between common motifs GYW and WGL in the IMGpep-4 sequence was substituted with "R(Arg)." Furthermore, biotinylated IMGpep-1CS (biotin-spacer-GSGYWRSEWGLSG (SEQ ID NO: 12)) was synthesized, in which two cysteine residues (C) in the IMGpep-1 sequence were substituted with serine (S). The synthetic peptides IMGpep-1 (GCGYWRSEWGLCG; SEQ ID NO: 7), IMGpep-4 (GCTGYWPKAWGLCG; SEQ ID NO: 9), IMGpep-1E6Q (GCGYWRSQWGLCG; SEQ ID NO: 10), IMGpep-4K6R (GCTGYWPRAWGLCG; SEQ ID NO: 11), and IMGpep-1CS (GSGYWRSEWGLSG; SEQ ID NO: 12) were synthesized by the Fmoc method and then purified with reverse phase columns. Subsequently, the N-terminal amino group thereof was biotinylated via biotinylation modification using Sulfo-NHS-LC-Biotin (Pierce).

The binding activity of the thus obtained biotinylated synthetic peptides to human IgG was assayed by an ELISA assay. The ELISA assay was conducted basically in a manner similar to that in Example 1. Specifically, wells coated with human IgG (100 ng/50 µl/well) were blocked by the addition of 0.5% BSA. A biotinylated synthetic peptide and alkaline phosphatase-labeled streptavidin (SA-AP) were mixed in advance at a molar ratio of 4:1 and then the mixture was added to the well, followed by 1 hour of reaction. Para-nitrophenyl phosphate (Wako) was used for color development. Detection was carried out by measuring absorbance at 405 nm. As a positive control of human IgG, the Fc fragment of hIgG was used. As other control proteins, human IgA and IgE, mouse IgG, IgA, and IgE, hTF, fetal bovine serum (FBS), HSA, BSA, and gelatin were used.

Figure 6:
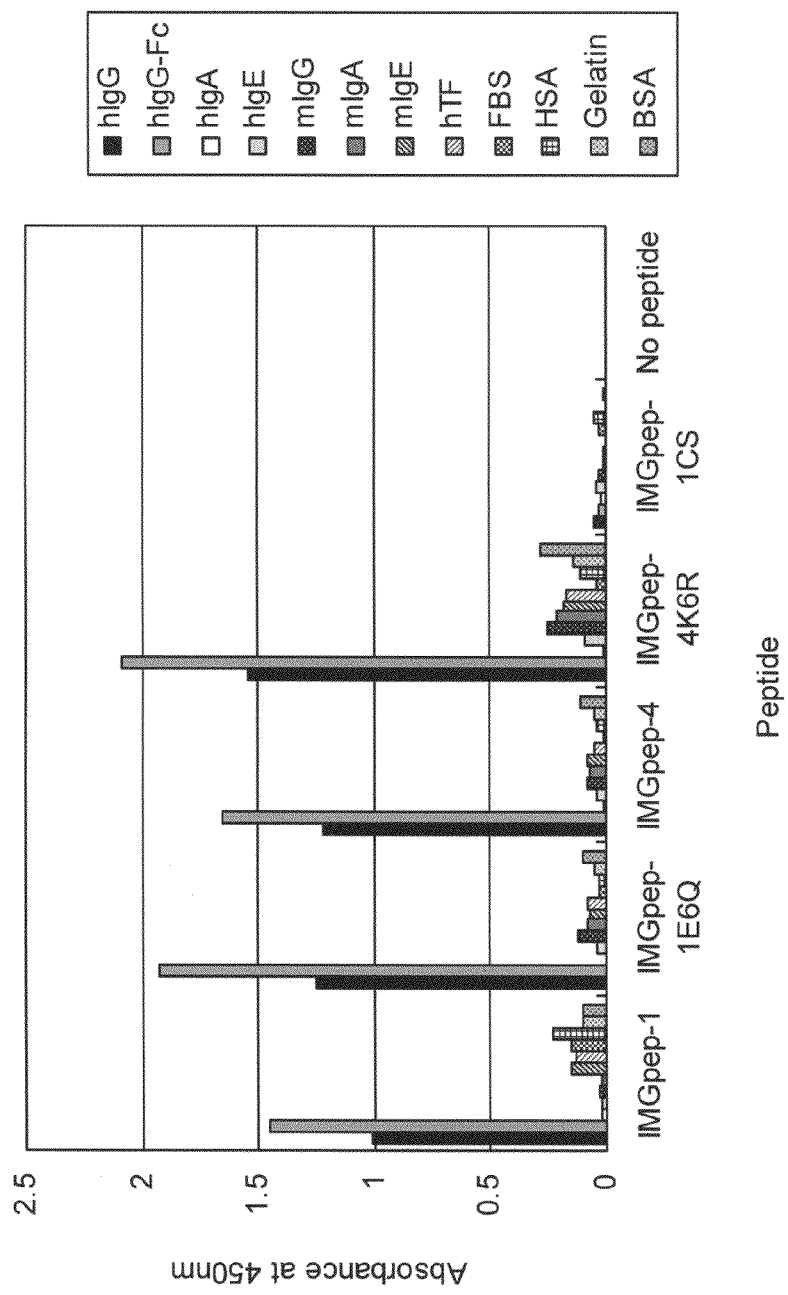
FIG. 6 shows the binding specificity of the human IgG-specific synthetic peptides to human IgG. The bars indicate, from the left, per each synthetic peptide, the property of binding to hIgG, hIgG-Fc, hIgA, hIgE, mIgG, mIgA, mIgE, hTF, FBS, HSA, gelatin, and BSA, respectively.

The results are shown in FIG. 6. It was shown that IMGpep-1 and IMGpep-4 specifically bound to human IgG in a manner similar to that of the phage clones G-1 to G-6 as described in the above Example and also bound to the Fc fragment of human IgG. It was further shown that the binding activity of IMGpep-1E6Q and IMGpep-4K6R in which one amino acid residue had been substituted significantly and drastically increased compared with the original peptides IMGpep-1 and IMGpep-4. On the other hand, IMGpep-1CS in which 2 cysteine residues had been substituted with serine residues was found to almost lose the binding activity to human IgG. It was thus shown that, similar to the phage clones G-1 to G-6, these synthetic peptides also need intramolecular disulfide bond formation for specific binding with IgG.

Figure 7:
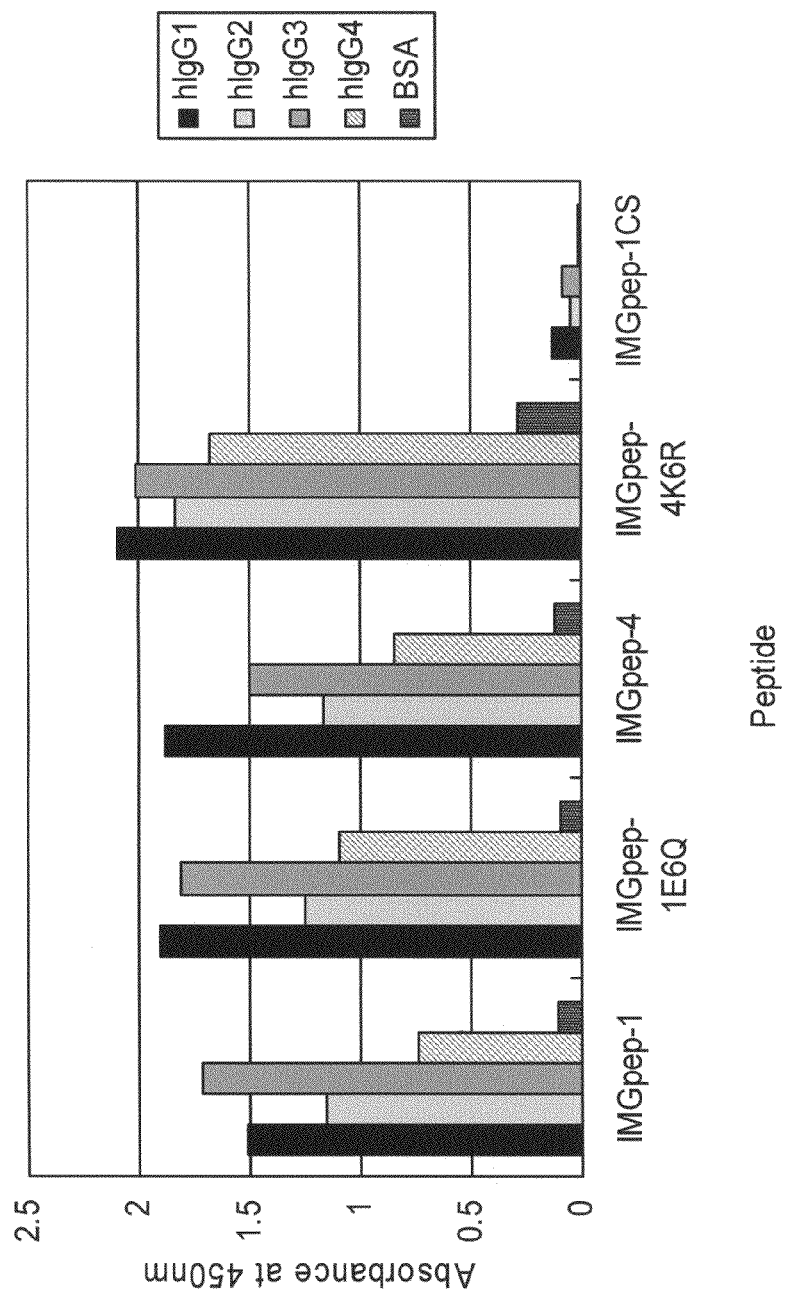
FIG. 7 shows the binding activity of human IgG-specific synthetic peptides to human IgG isotype antibodies. The bars indicate, from the left, per each synthetic peptide, the property of binding to hIgG1, hIgG2, hIgG3, hIgG4, and BSA, respectively.
Figure 8:
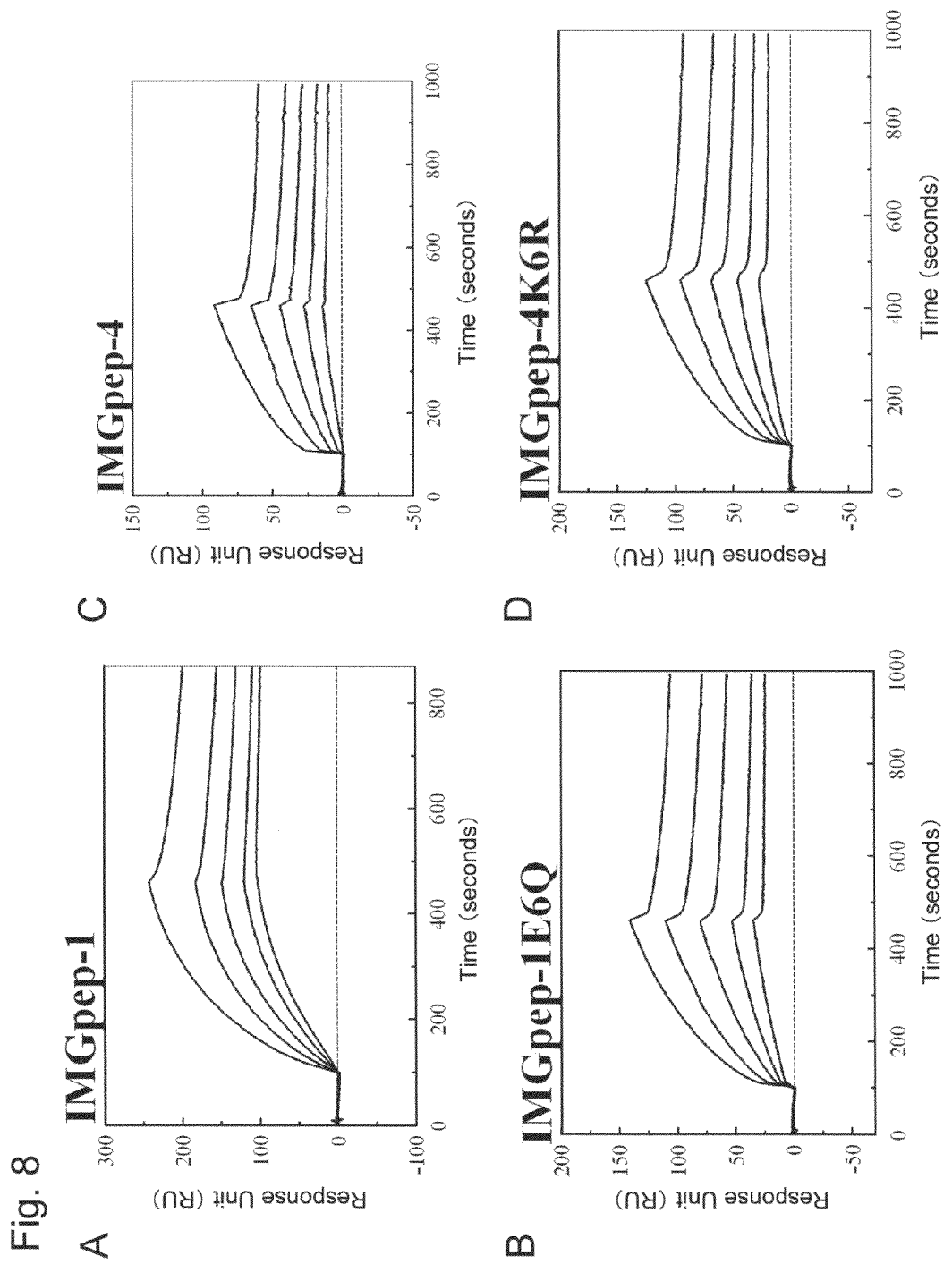
FIG. 8 shows the results of surface plasmon resonance analysis of the binding among various human IgG-specific synthetic peptides and human IgG. Horizontal axis represents time (seconds) and vertical axis represents response units (RUs).

Furthermore, the binding activity of the biotinylated synthetic peptides to human IgG isotypes (hIgG1 to hIgG4), was assayed similarly by an ELISA assay. As a control protein of human IgG, BSA was used. The results are shown in FIG. 7. IMGpep-1 and IMGpep-4 exhibited strong binding activity to all of human IgG1, IgG2, IgG3, and IgG4 in a manner similar to that of the phage clones G-1 to G-6 as described in the above Example. IMGpep-1E6Q and IMGpep-4K6R, in which one amino acid residue had been substituted, also exhibited strong binding activity to human IgG1 to IgG4, which was found to increase to a greater extent than that of IMGpep-1 and IMGpep-4. IMGpep-1CS was observed to almost completely lose its binding activity to IgG1 to IgG4.

The above results demonstrated that the synthetic peptides consisting of the peptide sequences identified in Example 1 or analogous sequences thereof containing the common motifs can specifically bind to a human IgG antibody (particularly, the Fc region).

Example 6

Kinetic Analysis of the Binding Between the Peptide of the Present Invention and Human IgG Binding between the synthetic peptide IMGpep-1, IMGpep-1E6Q, IMGpep-4, or IMGpep-4K6R and human IgG was subjected to kinetic analysis of binding using surface plasmon resonance (SPR). SPR analysis was carried out using BIAcore2000 (BIAcore) at 25° C. Necessary reagents and sensor chips were purchased from BIAcore and then used. A 50 µM solution (pH 5) of each of four biotinylated synthetic peptides (IMGpep-1, IMGpep1E6Q, IMGpep4, and IMGpep-4K6R) was injected over a sensor chip SA, so as to immobilize the peptide on the chip. The amount of each peptide to be immobilized was adjusted so that the RU (responce unit) ranged from 1500 to 2000. Subsequently, human IgG (analyte) was injected at a flow rate of 10 µl/min and at various concentrations (660 nM, 330 nM, 165 nM, 82 nM, and 41 nM) through flow cells with the aforementioned sensor chips SA on which the biotinylated-peptides had been immobilized. Binding reaction between human IgG and the peptides was measured. Thereafter, washing with running buffer (HBS-T) was conducted and then dissociation reaction was measured. For washing/elution of bound analytes from the sensor chips, 0.2 M glycine-HCl buffer (pH 2.7) was used. Binding parameters were analyzed using BIA evaluation Version 3.2 software.

Sensorgrams obtained via the above SPR analysis are shown in FIG. 8A to 8D. Dissociation constants (Kd) of the binding reaction between IMGpep-1, IMGpep-1E6Q, IMGpep4, or IMGpep-4K6R and human IgG were 17 nM, 21 nM, 28 nM, and 24 nM, respectively, as calculated from the sensorgrams. Moreover, the association rate constants (ka) were calculated to be $2.0 \times 10^4$ $M^{-1}sec^{-1}$, $1.5 \times 10^4$ $M^{-1}sec^{-1}$, $1.4 \times 10^4$ $M^{-1}sec^{-1}$, and $1.6 \times 10^4$ $M^{-1}sec^{-1}$, respectively. The dissociation rate constants (kd) were calculated to be $3.4 \times 10^{-4}$ $sec^{-1}$, $3.1 \times 10^{-4}$ $sec^{-1}$, $4.1 \times 10^{-4}$ $sec^{-1}$, and $3.8 \times 10^{-4}$ $sec^{-1}$, respectively.

Meanwhile, when biotinylated IMGpep-1CS, in which cysteine residues had been substituted with serine residues in IMGpep-1 so as to avoid circularization due to disulfide bond formation, was immobilized on a sensor chip and used as a control ligand and then human IgG was injected as an analyte through a flow cell, an increased response signal due to the binding was never observed.

Example 7

Immunoprecipitation of Human IgG Using the Peptide of the Present Invention as a Tag Synthetic peptides IMGpep-1 (GCGYWRSEWGLCG; SEQ ID NO: 7) and IMGpep-2 (GCTGFWEREWGLCG; SEQ ID NO: 8) were designed based on the amino acid sequences of the peptides displayed by the phage clones G-1 and G-2, synthesized by the Fmoc method, purified using reverse phase columns, and then used for the following experiment.

The above cloned T7 phage G-1 ($1.0 \times 10^{12}$ pfu) subjected to ultracentrifuge purification or a synthetic peptide IMGpep-1 (150 nmol) was immobilized on 3 mg of tosyl-activated M450 Dynabeads magnetic beads (Dynal) via covalent binding to the terminal amino group according to the protocols recommended by the manufacturer. The beads were blocked with a PBS solution containing 0.5% BSA and then added to 1 ml of hIgG/BSA/PBS (10 µg/ml hIgG and 1 mg/ml BSA), followed by 1 hour of reaction at room temperature while mixing the solution via stirring. Beads were washed 3 times with PBST, SDS-sample buffer was added thereto, and then SDS-PAGE fractionation was carried out. Subsequently, they were subjected to western blotting analysis using a biotinylated anti-hIgG goat polyclonal antibody (Goat Anti-hIgG-pAb-biotin; Pharmingen) and SA-HRP, and then human IgG immunoprecipitated by binding to beads was detected.

Furthermore, immunoprecipitation reaction was similarly carried out using phage clones G-1 415 or IMGpep-2 instead of phage G-1 or IMGpep-1 to detect human IgG. Here, the phage clone G-1 415 (Novagen) is a phage displaying G-1 peptide at all the 415 G10 proteins composing the capsid of T7 phage. Moreover, immunoprecipitation reaction and detection were similarly carried out using an anti-hIgG goat (Fab')₂ fragment, wild-type T7 phage, and BSA, as a control of phage G-1 or IMGpep-1.

Figure 9:
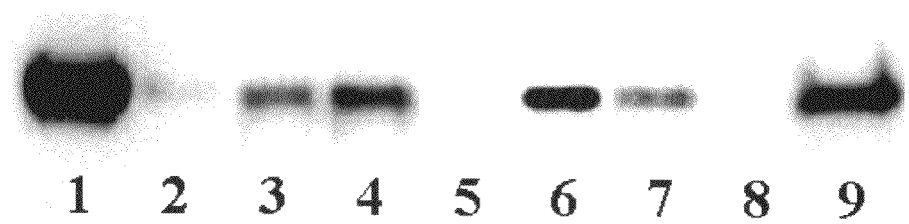
FIG. 9 is a photograph showing the results of immunoprecipitation of human IgG antibodies using magnetic beads on which human IgG-specific synthetic peptides and human IgG specific phage clones were each immobilized.

The results are shown in FIG. 9. In FIG. 9, lane 1; anti-hIgG goat (Fab')₂ fragment, lane 2; wild-type T7 phage, lane 3; phage G-1, lane 4; phage G-1 415, lane 5; BSA, lane 6; IMGpep-1, and lane 7; IMGpep-2. To lanes 8 and 9, BSA and human IgG were directly applied as controls, respectively.

As shown in FIG. 9, whereas no immunoprecipitated human IgG was observed in the case of beads on which wild-type T7 phage or BSA had been immobilized, immunoprecipitated human IgG was clearly observed in the case of beads on which phage G-1, phage G-1 415, IMGpep-1, or IMGpep-2 had been immobilized. Also, when beads on which phage G-1 415 had been immobilized were used, compared with the case of phage G-1, human IgG was detected at a higher level. This indicated that the phage G-1 415 displaying G-1 peptide at all the 415 G10 proteins trapped and immunoprecipitated human IgG in numbers increased depending on the number of G-1 peptides displayed. Furthermore, the synthetic peptide IMGpep-1 exhibited human IgG trapping efficiency clearly higher than that of IMGpep-2. The human IgG binding level of IMGpep-1 or IMGpep-2 as revealed by immunoprecipitation assay correlated with the IgG-binding activity of the phage clone G-1 or G-2 (based on which those synthetic peptide sequences had been synthesized), as confirmed by the ELISA assay. For the lane of a case in which empty beads to which none had been immobilized were used, no human IgG was detected.

The above results showed that human IgG can be specifically immunoprecipitated using the synthetic peptides above.

Example 8

Effects of Acid Treatment in Immunoprecipitation of Human IgG Using the Peptide of the Present Invention 4 mg of streptavidin-M280 Dynabeads, magnetic beads (Dynal) was mixed with 400 µl of biotinylated synthetic peptide IMGpep-4K6R (100 nmol) for immobilization and then a PBS solution containing 0.5% BSA was added for blocking.

Meanwhile, hIgG (pH 2.2 at the time of elution) which had been purified from human serum with SpA sepharose beads (Amersham Pharmacia Biotech), a polyclonal human IgG (hIgG) antibody (Sigma), an anti-IL-6 receptor MRA (humanized anti-interleukin 6 receptor monoclonal antibody, Chugai Pharmaceutical), an anti-HER2 human antibody (Herceptin) or human serum was treated in a 0.1 M glycine-HCl solution (pH 1.5) for 5 minutes. Tris was then added to neutralize the pH. To the thus acid-treated samples (an antibody sample was prepared in a 10 µm/ml PBS solution containing 1 mg/ml BSA and a human serum sample was prepared in 1:20 dilution of a PBS solution), 0.2 mg of beads blocked as described above was added, and then reaction was carried out while mixing the resultant with stirring at room temperature for 1 hour. After reaction, beads were collected and then washed 3 times with PBST. SDS-sample buffer was added, SDS-PAGE was carried out, and then the gel was subjected to CBB staining, so that immunoprecipitated hIgG was visualized. As a control experiment, the same reaction was carried out using the same antibody and serum sample, and a polyclonal mouse IgG antibody without acid treatment (untreated). Moreover, a similar control experiment was conducted using empty beads to which biotinylated IMGpep-4K6R had not been immobilized.

Figure 10:
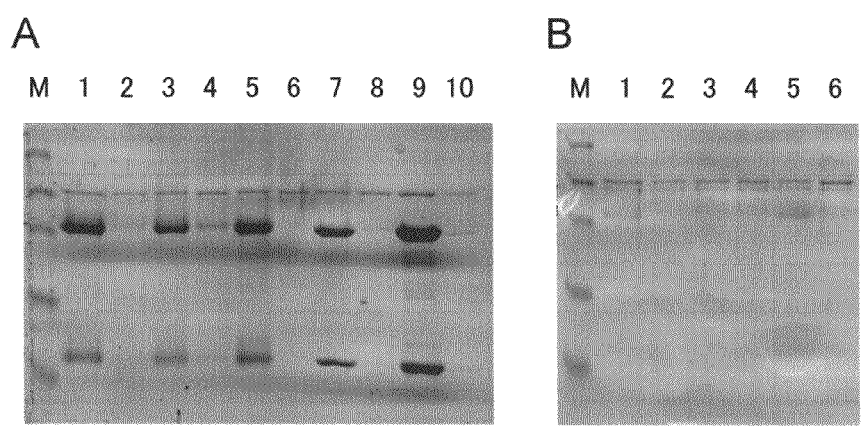
FIG. 10 shows photographs showing the results of immunoprecipitation of hIgG antibodies after acid treatment, using human IgG-specific synthetic peptides.

The results are shown in FIG. 10. In FIG. 10A, M; molecular weight markers (83, 62, 47, 32, and 25 kDa), lane 1; hIgG (pH 2.2 at the time of elution) purified with SpA sepharose beads from human serum, lane 2; untreated polyclonal hIgG antibody, lane 3; acid-treated polyclonal hIgG antibody, lane 4; untreated anti-IL-6 receptor MRA, lane 5; acid-treated anti-IL-6 receptor MRA, lane 6; untreated anti-HER2 human antibody (Herceptin), lane 7; acid-treated anti-HER2 human antibody (Herceptin), lane 8; untreated human serum, lane 9; acid-treated human serum, and lane 10; polyclonal mouse IgG antibody. FIG. 10B shows the results of reacting empty streptavidin M280 Dynabeads magnetic beads on which no biotinylated peptide had been immobilized and biotin alone had been reacted therewith the above-mentioned antibodies or serum samples. In FIG. 10B, M; molecular weight markers (83, 62, 47, 32, and 25 kDa), lane 1; hIgG (pH 2.2 at the time of elution) purified with SpA sepharose beads from human serum, lane 2; acid treated polyclonal hIgG antibody, lane 3; acid-treated anti-IL-6 receptor MRA, lane 4; acid-treated anti-HER2 human antibody (Herceptin), lane 5; acid-treated human serum, and lane 10; polyclonal mouse IgG antibody.

As shown in FIG. 10, as a result of acid treatment, for all the prepared samples containing hIgG, the recovered amounts of hIgG with the use of beads on which the peptide of the present invention had been immobilized were significantly increased. On the other hand, no hIgG was recovered with the use of empty beads on which no peptide had been immobilized. This suggests that the increased recovery rates of acid-treated antibodies are not due to the enhanced degree of non-specific adsorption to beads.

The above results showed that immunoprecipitation of human IgG with the peptide of the present invention can be accelerated by acid treatment of human IgG.

The results of this Example also showed that the peptides of the present invention specifically bind to human IgG having a specific conformation that can be induced by acid treatment. Specifically, the peptide of the present invention can specifically recognize the Fc region of human IgG in an acid-denatured form. As shown FIG. 10, human IgG having such specific conformation (i.e., in an acid-denatured form) was almost never detected in untreated human serum, but contained to some extent in commercial antibody reagents or antibody drugs.

In view of this Example, it was considered that human IgG found (in the above Examples 1 to 7) to bind to the peptides of the present invention or phage clones displaying the peptides had the same conformation as that induced by acid treatment.

Example 9

Generation of Acid-Denatured Human IgG Under Various Acid Treatment Conditions

As factors having influence on the generation of acid-denatured human IgG, i.e., a human IgG conformer having a conformation to be induced under acidic conditions (acid-denatured conformation), particularly pH and temperature were studied in detail. In this study, to evaluate the content of molecular species having an acid-denatured conformation, a biotinylated IMGpep-4K6R peptide (biotin-spacer-GCTGY-WPRAWGLCG) and a biotinylated Fc-III peptide (biotin-spacer-DCAWHLGELVWCT; see Non-patent Document 8 for the Fc-III peptide) were each immobilized on a surface plasmon resonance spectrum (SPR) sensor chip in a manner similar to that in Example 2.

Next, an acid-treated IgG sample was separately injected at a flow rate of 20 μl/min through a flow cell with the sensor chip on which the biotinylated IMGpep-4K6R had been immobilized and through a flow cell with the sensor chip on which the biotinylated Fc-III peptide had been immobilized. Binding reaction on the sensor chips was measured.

The response value on the sensor chip on which the biotinylated IMGpep-4K6R had been immobilized indicates the content of acid-denatured human IgG. Meanwhile, Fc-III peptide recognizes human IgG having an undenatured conformation that is obtained under neutral conditions, but at the same time recognizes acid-denatured human IgG that is induced under acidic conditions. Accordingly, the SPR response value on the sensor chip on which biotinylated Fc-III peptide had been immobilized represented the level of all the antibodies in an IgG sample injected for SPR.

Hence, the content of acid-denatured human IgG in a human IgG sample after acid treatment was evaluated via calculation of the ratio of SPR response value on the sensor chip on which the biotinylated IMGpep-4K6R had been immobilized to SPR response value on the sensor chip on which the biotinylated Fc-III peptide had been immobilized, indicating the generation rate of acid-denatured human IgG.

For this SPR analysis, human IgG samples were prepared via acid treatment under various conditions as described below and then tested. First, each reaction solution (IgG 40 μg/ml, 250 nM) was prepared by adding 20 μl of 1 M glycine-HCl with varied pHs (1.5, 2.1, and 2.7) to 80 μl of an anti-HER2 human antibody (125 μg/ml, 0.1M NaCl solution), followed by 10 minutes of incubation at various temperatures (20° C., 30° C., and 40° C.). Subsequently, 30 μl (or 20 μl for a sample to which glycine-HCl with pH 2.7 had been added) of 1 M Tris-HCl (pH 8.7) was added to each solution for neutralization. After neutralization, each antibody solution was diluted with running buffer to 250 nM and then injected over a sensor chip for SPR analysis. pH of the solution was confirmed with pH test strips after neutralization and before injection over sensor chips.

Figure 11:
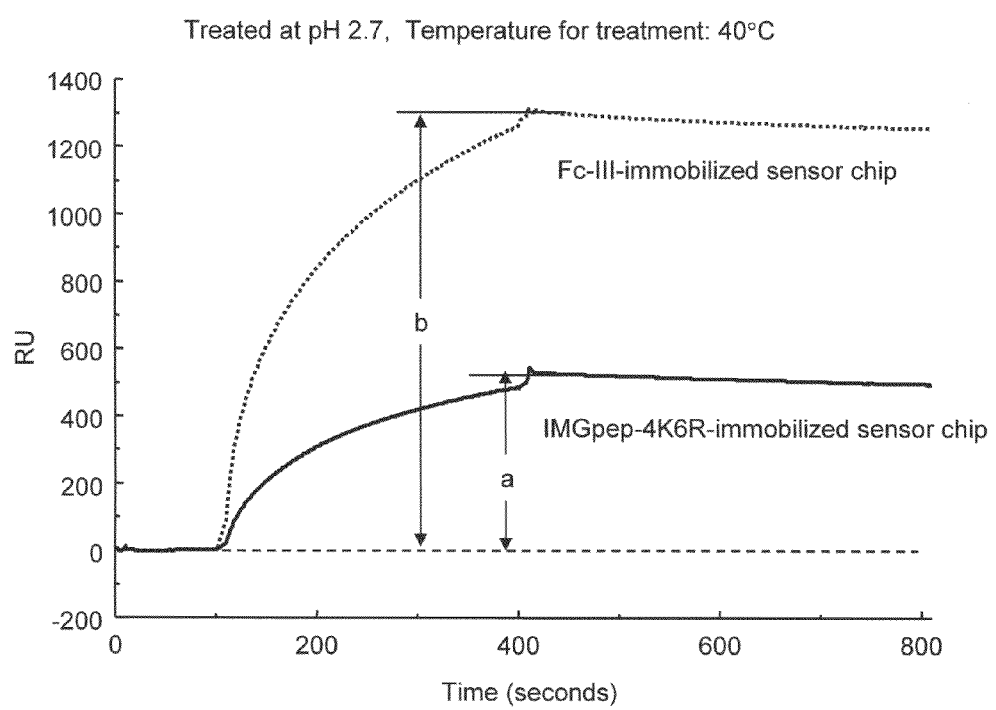
FIG. 11 exemplifies SPR sensorgram showing the reactivity of an IgG sample after acid treatment (treated at pH 2.7 and at a temperature of 40° C.) to peptide Fc-III or IMGpep-4K6R immobilized on a sensor chip. Horizontal axis represents time (seconds) and vertical axis represents response units (RUs). Based on the ratio of "a" to "b" (a/b) as shown in FIG. 11, the generation rate of IgG having an acid-denatured conformation (acid-denatured IgG) were calculated.

FIG. 11 shows the SPR sensorgram as an example showing the reactivity between the human IgG samples subjected to acid treatment at pH 2.7 and 40° C. and the Fc-III peptide or IMGpep-4K6R. Based on the ratio of "a" to "b" (a/b) as shown in FIG. 11, the generation rate of acid-denatured IgG was calculated.

Figure 12:
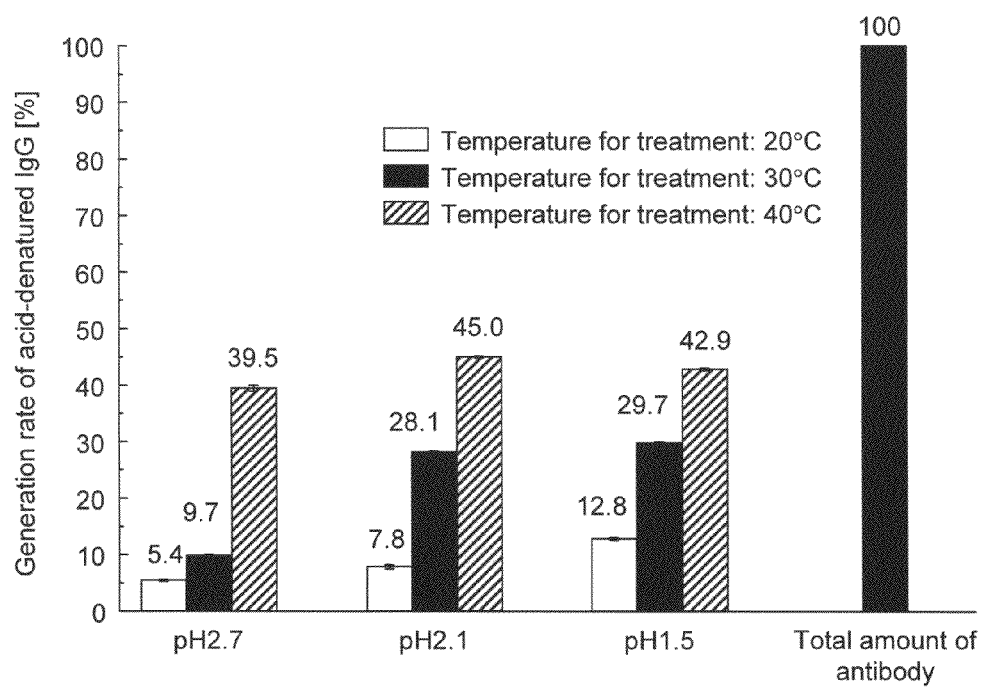
FIG. 12 shows changes in the percentage of the generation of acid-denatured human IgG depending on acid treatment conditions.

The results of determining the generation rates of acid-denatured IgG under various acid treatment conditions are summarized in FIG. 12. When acid treatment was carried out at pH 2.7 and 20° C., the generation rate of acid-denatured IgG was approximately 5%, however, when the pH was lowered to 2.1 and further lowered to 1.5, the generation rate was observed to slightly increase to 7.8% and 12.8%, respectively. On the other hand, in the case of treatment at pH 2.7, when the temperature for treatment was increased from 20° C. to 30° C., and then to 40° C., the resulting generation rate was drastically increased to 9.7% and 40%, respectively. The generation rate at 40° C. did not significantly change even when the pH was lowered to 2.1 and then to 1.5 and was kept to be approximately 40%. Accordingly, it was shown that the generation rate of acid-denatured IgG has a higher sensitivity to differences in temperature than to those in pH, at least within the pH range (pH 1.5 to 2.7), although it is affected by pH differences as well as temperature differences.

Example 10

Separation of Acid-Denatured IgG in Acid-Treated IgG Sample

Next, separation of acid-denatured IgG from undenatured IgG in a human IgG sample acid-treated was carried out using a column on which IMGpep-4K6R had been immobilized.

An antibody sample was prepared, as described in Example 9, by acid treatment of an anti-HER2 human antibody (Herceptin) under conditions of pH2.7, 40° C., and 10 minutes of incubation. Moreover, a biotinylated IMGPep-4K6R peptide (biotin-spacer-GCTGYWPRAWGLCG (SEQ ID NO: 11)) solution (500 μM, 1 ml) was injected to a HiTrap Streptavidin HP column (GE Healthcare) to prepare the column in which IMGPep-4K6R was immobilized. The antibody sample was injected at a flow rate of 0.4 ml/min to the IMGPep-4K6R-immobilized column. Gradient elution was carried out using from 20 mM phosphate buffered saline (PBS, pH 7.0) containing 0.1 M NaCl to 0.1M glycine-HCl (pH 2.5) containing 0.1 M NaCl. The results are shown in FIG. 13.

Figure 13:
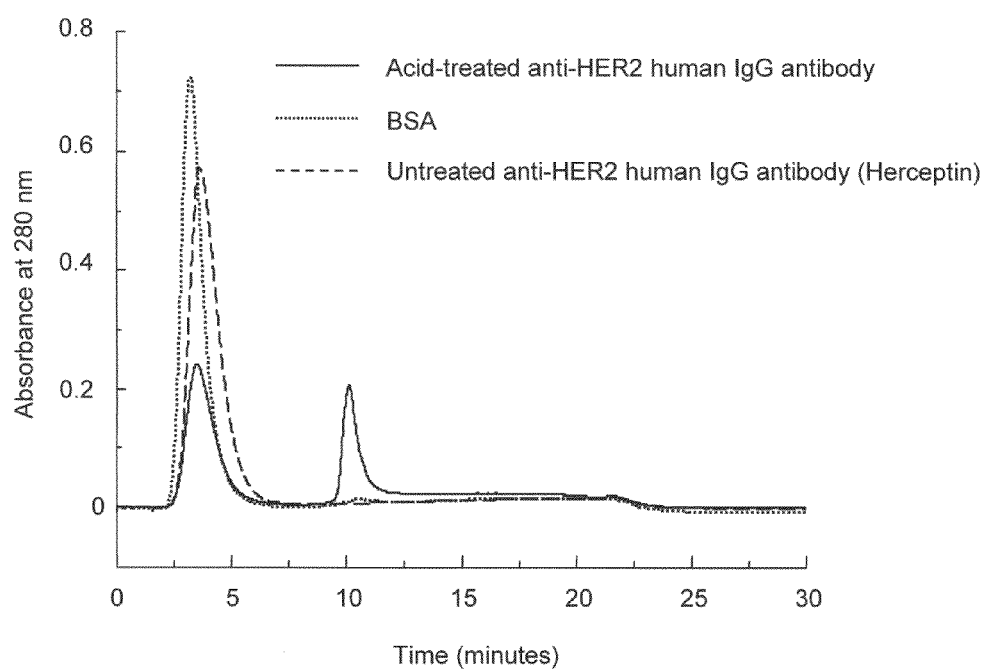
FIG. 13 shows the separation of acid-denatured human IgG with an IMGpep-4K6R-immobilized column.

As shown in FIG. 13, whereas the untreated anti-HER2 human IgG sample thought to mainly have an undenatured (native) conformation passed through the IMGpep-4K6R-immobilized column, approximately 35% of IgG in the acid-treated anti-HER2 human IgG sample was adsorbed to the column and then eluted via acid gradient elution for approximately 10 minutes of elution. Most of the thus eluted IgGs was thought to be anti-HER2 human IgGs having an acid-denatured conformation.

Example 11

Characterization of Acid-Denatured Anti-HER2 Human IgG Separated Using the Peptide of the Present Invention The acid-denatured anti-HER2 human IgG eluted in Example 10 was isolated and was immediately neutralized with 1M Tris-HCl buffer (pH 8.7), and then dialyzed against PBS. The thus obtained purified IgG sample was subjected to characterization.

Figure 14:
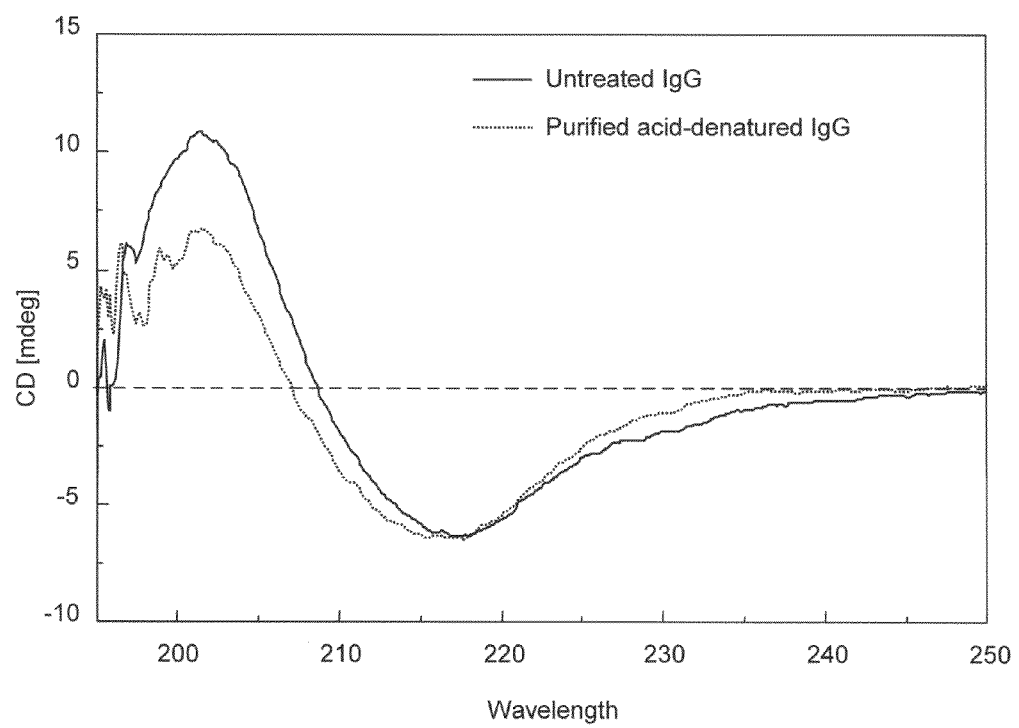
FIG. 14 shows the CD spectrum of human IgG having an acid-denatured conformation (acid-denatured human IgG). A continuous line indicates untreated IgG and a dashed line indicates purified acid-denatured IgG.

FIG. 14 shows the circular dichroism spectrum (CD spectrum) measured for the purified sample. Acid-denatured human IgG showed an increased absorption maximum around 205 nm compared to untreated human IgG and thus it was presumed that the content of the random structure was increased therein. On the other hand, the intensity of the negative absorption around 215 nm due to the β-sheet structure of immunoglobulin domains was almost equivalent to that of untreated human IgG. Therefore, it was considered that in acid-denatured human IgG, random structures increased, while most of β-sheet structures of the entire antibody were retained.

Example 12

Removal of Acid-Denatured IgG Using the Peptide of the Present Invention

Humanized anti-human IL-6 receptor monoclonal IgG antibody (MRA; general name; tocilizumab, Chugai Pharmaceutical) was subjected to acid treatment, and MRA having acid-denatured conformation (acid-denatured MRA) was separated from the resulting sample, followed by analyzing the apparent molecular weight of the separated MRA by molecular sieve chromatography.

First, 20 μl of 1 M glycine-HCl (pH 2.7) was added to 200 μl of humanized anti-human IL-6 receptor IgG antibody (MRA) (2000 μg/ml, PBS solution). The solution was incubated for 10 minutes at 30° C. and then 30 μl of 1 M Tris-HCl (pH 8.7) was added thereto for neutralization to prepare an acid-treated antibody sample. Also, a biotinylated IMGPep-4K6R peptide-immobilized column was prepared in a manner similar to that in Example 10. An acid-treated antibody sample was injected at a flow rate of 0.4 ml/min to the column and then gradient elution was carried out using from 20 mM phosphate buffered saline (PBS, pH 7.0) containing 0.1M NaCl to 0.1M glycine-HCl (pH 2.5) containing 0.1M NaCl. The thus eluted IgG was a purified acid-denatured humanized anti-human IL-6 receptor IgG antibody (MRA).

Subsequently, the purified acid-denatured MRA was subjected to molecular sieve chromatography using a HiLoad Sperdex 200 16/60 column (GE Healthcare). Similarly, untreated MRA, an acid-treated antibody sample, and a flow-through fraction (undenatured MRA) obtained via injection of an acid-treated antibody sample to a biotinylated IMGPep-4K6R peptide-immobilized column, were also separately subjected to molecular sieve chromatography using a HiLoad Sperdex 200 16/60 column (GE Healthcare). Elution from such columns was carried out at a flow rate of 1.0 ml/min using 50 mM phosphate buffer (pH 7.0) containing 0.15 M NaCl. The results are shown in FIG. 15.

Figure 15:
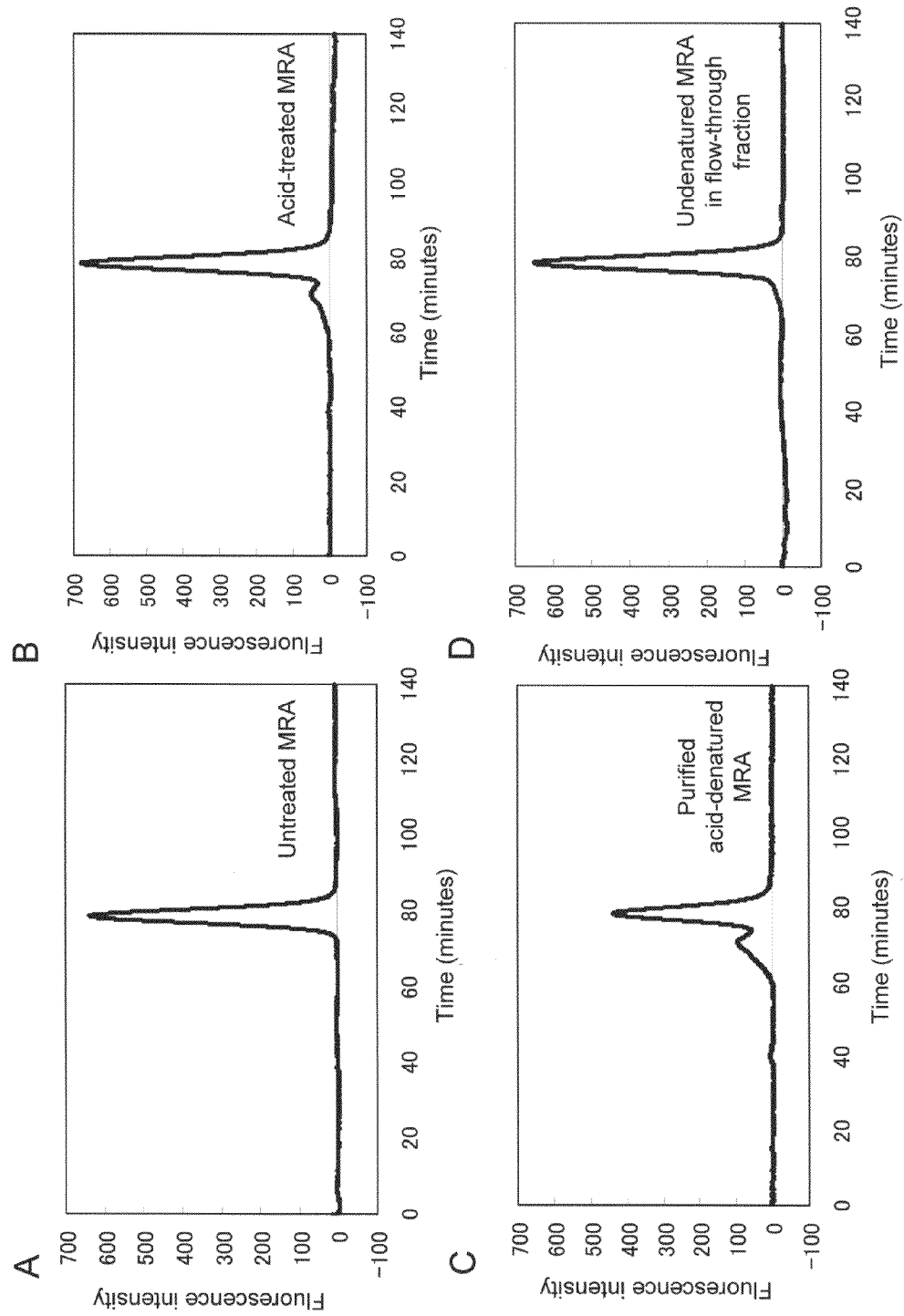
FIG. 15 shows the results of molecular sieve chromatography of acid-denatured human anti-IL-6 receptor antibody, MRA.

As shown in FIG. 15, almost all the untreated human anti-IL-6 receptor antibodies MRA were monomeric IgGs (FIG. 15A). Meanwhile, in the acid-treated antibody samples, peaks of dimers or trimers that are more rapidly eluted than monomers were produced slightly, suggesting that oligomerization of IgG antibodies was caused by acid treatment (FIG. 15B).

The peak of oligomers was found to increase in the purified acid-denatured MRA (FIG. 15C), indicating that dimers or trimers were contained at greater levels. However, on the other hand, approximately 65% of purified acid-denatured MRAs were still monomers, showing that acid-denatured MRA does not form any aggregate due to the progress of denaturation (FIG. 15C).

Furthermore, almost no oligomer was observed in a flow-through fraction obtained by passing the acid-treated antibody sample through the IMGPep-4K6R peptide-immobilized column (FIG. 15D).

These results showed that, by the use of the biotinylated IMGpep-4K6R-immobilized column, human IgG MRA having an acid-denatured conformation and particularly an oligomer thereof can be efficiently removed from an antibody sample.

Hence, next, as performed in Example 10, a test was conducted to confirm whether or not an acid-denatured IgG could actually be sufficiently removed from an antibody sample by dividing an acid-treated human IgG sample into an acid-denatured IgG fraction and an undenatured IgG fraction via IMGPep-4K6R-immobilized column chromatography. An immunoprecipitation experiment using an IMGpep-4K6R peptide was conducted by a method similar to that employed in Example 8 for each of an untreated MRA sample, an acid-treated MRA sample (acid treated for 10 minutes at pH 2.2 and 4° C.), a flow-through fraction obtained by passing an acid-treated MRA sample through a biotinylated IMGPep-4K6R peptide-immobilized column, and a purified acid-denatured MRA sample (an adsorbed fraction obtained by passing a human IgG sample subjected to 10 minutes of acid treatment at pH 2.2 and 4° C. through an IMGpep-4K6R peptide-immobilized column). IgG precipitated with the peptide immobilized on magnetic beads was subjected to 12.5% SDS-PAGE and then to CBB staining, and then observed. The results are shown in FIG. 16.

Figure 16:
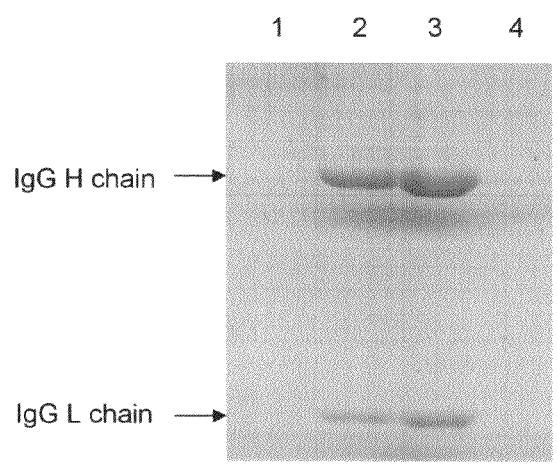
FIG. 16 shows the experimental results of immunoprecipitation with IMGpep-4K6R peptide-immobilized beads, from fractions separated from acid-treated human IgG samples via column chromatography using an IMGep-4K6R peptide-immobilized column. Lane 1; Untreated antibody, MRA. Lane 2; Sample of antibody MRA treated at pH 2.2 and 4° C. for 10 minutes. Lane 3; Purified acid-denatured MRA (an adsorbed fraction obtained by passing an antibody MRA sample treated at pH 2.2 and 4° C. for 10 minutes through an IMGpep-4K6R peptide-immobilized column). Lane 4; A flow-through fraction obtained by passing an antibody MRA sample treated at pH 2.2 and 4° C. for 10 minutes through a biotinylated IMGPep-4K6R peptide-immobilized column.

As shown in FIG. 16, the untreated MRA antibody was not immunoprecipitated by the IMGpep-4K6R peptide (lane 1). However, it was clearly shown that acid-treated MRA (lane 2) and purified acid-denatured MRA (lane 3) contained IgG having an acid-denatured conformation. On the other hand, immunoprecipitation was never observed in the flow-through fraction (lane 4, the same fraction as that in FIG. 15D). The results suggest that acid-denatured IgG was sufficiently removed from the flow-through fraction with the use of the IMGpep-4K6R peptide-immobilized column.

Example 13

Measurement of Acid-Denatured IgG Contents in Commercial IgG Products

For several commercial antibody drugs, immunoglobulin preparations and the like, the content of human IgG having an acid-denatured conformation was evaluated using a method similar to that disclosed in Example 9. Specifically, human IgG solutions of antibody drugs, immunoglobulin preparations, and the like adjusted at 40 μg/ml were each injected through a flow cell with an SPR sensor chip on which IMGpep-4K6R and Fc-III peptides had been separately immobilized. Binding reaction on the sensor chip was measured. The acid-denatured IgG content (%) was calculated from the ratio (a/b) of the response value "a" of the cell on which the IMGpep-4K6R peptide had been immobilized to the response value "b" of the cell on which the Fc-III peptide had been immobilized.

Figure 17:
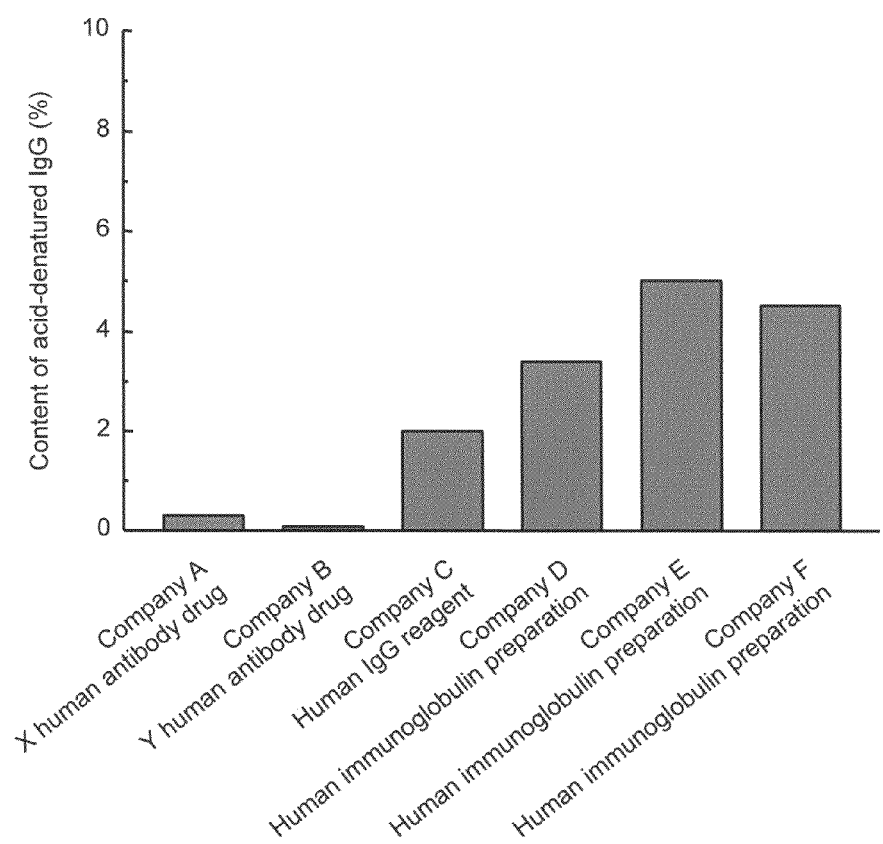
FIG. 17 shows the contents (%) of acid-denatured human IgG relative to the total amounts of IgG in human IgG antibody drugs or immunoglobulin preparations.

As shown in FIG. 17, both the examined two antibody drugs (in FIG. 17, Company A-human antibody drug X and Company B-human antibody drug Y) had acid-denatured IgG contents of as low as less than 0.5%. On the other hand, the immunoglobulin preparations had each acid-denatured IgG contents of as high as more than 3%. It was considered that this difference is due to different human IgG purification methods employed for manufacture of these preparations.

Example 14

Study of the IgG Detection Sensitivity of the Peptide of the Present Invention

Acid-treated human MRA (IgG) was detected on the membrane using IMGpep-4K6R (the peptide of the present invention) and the IMGpep-1CS peptide. Specifically, acid-treated human MRA (IgG) and untreated human MRA (IgG) were spotted on nitrocellulose membranes in an amount of 1.5 ng, 3 ng, 6 ng, 12.5 ng, 25 ng, 50 ng, and 100 ng per spot. The membranes were dried for 5 minutes and then 0.5% BSA was added for blocking for 2 hours at room temperature. Here, acid-treated human MRA was prepared by adding 10 μl of 1 M glycine-HCl (pH 2.8) to 100 μl of humanized anti-human IL-6 receptor IgG antibody (MRA) (2000 μg/ml, PBS solution), carrying out incubation at 40° C. for 10 minutes, and then neutralizing it by the addition of 30 μl of 1 M Tris-HCl (pH 8.7).

Figure 18:
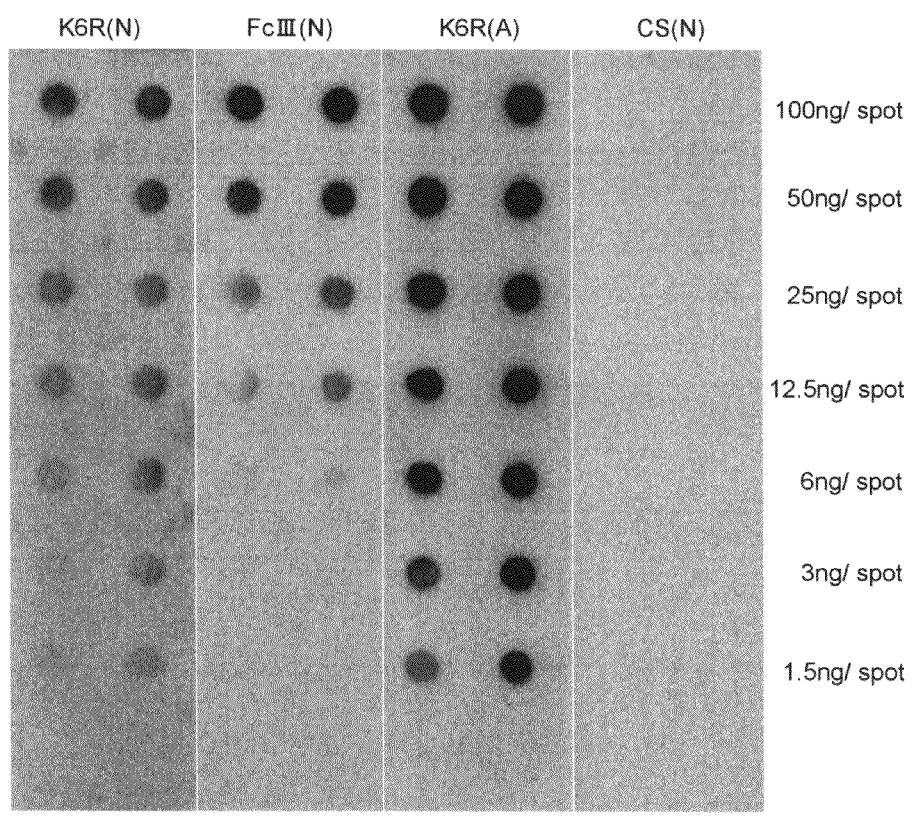
FIG. 18 is a photograph showing the results of detection with dot blotting of acid-treated IgG (human MRA) using the IMGpep-4K6R peptide (anti-human IgG peptide) of the present invention.

A biotinylated IMGpep-4K6R peptide or a biotinylated Fc-III peptide, or IMGpep-1CS, were mixed with HRP-conjugated SA (streptavidin) (120 nM) in advance at a molar ratio of 4:1. The mixture was added to the membranes blocked as described above, followed by 1 hour of reaction. After 3 times of washing with PBS containing 0.1% Tween20, a chemiluminescence reagent (Chemi-Lumi One, Nakalai Tesque) was added. Images were analyzed for detection using a LAS-1000 Image Analyzer (Fuji Film). The results are shown in FIG. 18.

The detection using blotting of untreated human MRA (IgG) showed that the IMGpep-4K6R peptide could detect even 1.5 ng/ml spot, however, the overall signal intensity of the detected spots was observed to be significantly weak (see K6R(N)). When the Fc-III peptide was used for detecting the same untreated MRA sample, whereas high detection intensity could be obtained for the spots with high concentrations of IgG the detection limit was still 6 ng/spot (see Fc-III(N)). On the other hand, in the case of the detection using an antibody sample (see K6R(A)) that had become rich in acid-denatured IgG as a result of acid treatment, the IMGpep-4K6R peptide exhibited greatly enhanced IgG-detection sensitivity as well as IgG-detection intensity, and thus could sufficiently detect a 1.5 ng/ml antibody sample. In addition, an IMGpep-1CS peptide as a control could not detect any spots of untreated human MRA (IgG).

As described above, the human IgG detection sensitivity of the peptide of the present invention could be greatly enhanced due to acid treatment. The results showed that the method for detecting a human IgG antibody using acid treatment and the peptide of the present invention has very high sensitivity and useful.

All the publications, patents, and patent applications in their entireties that have been referred to in this application are hereby incorporated by reference into this application.

INDUSTRIAL APPLICABILITY

The peptide tag of the present invention can capture with high efficiency human IgG or an Fc region-containing fragment thereof and thus can be used for a method for detecting, purifying, or separating human IgG. In particular, the peptide tag of the present invention can be used for detection or removal of acid-denatured human IgG.

Sequence Listing Free Text

SEQ ID NOS: 1 to 12 and 15 to 16 are synthetic peptides.
SEQ ID NOS: 13 to 14 are primers.

The invention claimed is:

1. A human IgG binding peptide tag that is 11 to 16 amino acids in length, comprising at least an amino acid sequence of formula I:

C-(X)$_n$-W-X-X-X-W-(X)$_m$-C  (I) (SEQ ID NO: 17)

wherein n and m are each an integer of 1 or more and the sum n+m is 4 or 5, wherein X-X-X in the formula I contains no cysteine residue, and
wherein said amino acid sequence satisfies either or both of a) and b):
 a) (X)$_n$-W in the formula I is Za-G-Y-W (SEQ ID NO: 18); and
 b) W-(X)$_m$ in the formula I is W-G-L-Zb (SEQ ID NO: 19)
wherein Za and Zb are each 0, 1, or more amino acid residues.

2. The peptide tag according to claim 1, wherein said amino acid sequence of the formula I satisfies both a) and b):
 a) (X)$_n$-W in the formula I is Za-G-Y-W (SEQ ID NO: 18); and
 b) W-(X)$_m$ in the formula I is W-G-L-Zb (SEQ ID NO: 19)
wherein Za and Zb are each 0, 1, or more amino acid residues.

3. The peptide tag according to claim 1, which consists of any of the amino acid sequences 1) to 11):

```
1) CGYWRSEWGLC;       (SEQ ID NO: 1)
2) CTGFWEREWGLC;      (SEQ ID NO: 2)
3) CLYWPRLWGLC;       (SEQ ID NO: 3)
4) CTGYWPKAWGLC;      (SEQ ID NO: 4)
5) CYWAVRWGLLGC;      (SEQ ID NO: 5)
6) CGYWADVWQIHC;      (SEQ ID NO: 6)
7) GCGYWRSEWGLCG;     (SEQ ID NO: 7)
8) GCTGFWEREWGLCG;    (SEQ ID NO: 8)
9) GCTGYWPKAWGLCG;    (SEQ ID NO: 9)
10) GCGYWRSQWGLCG;    (SEQ ID NO: 10)
and
11) GCTGYWPRAWGLCG    (SEQ ID NO: 11).
```

4. The peptide tag according to any claim 1, wherein a disulfide bond is formed between two cysteine residues in formula I.

5. The peptide tag according to claim 1, which binds to acid-denatured human IgG.

6. A human IgG binding peptide tag that is 11 to 16 amino acids in length, comprising at least an amino acid sequence of formula I:

C-(X)$_n$-W-X-X-X-W-(X)$_m$-C  (I) (SEQ ID NO: 17)

wherein n and m are each an integer of 1 or more and the sum n+m is 4 or 5, wherein X-X-X in the formula I contains no cysteine residue,
wherein said amino acid sequence satisfies either or both of a) and b):
 a) (X)$_n$-W in the formula I is Za-G-Y-W (SEQ ID NO: 18); and
 b) W-(X)$_m$ in the formula I is W-G-L-Zb (SEQ ID NO: 19)
wherein Za and Zb are each 0, 1, or more amino acid residues, and
wherein said peptide tag has been attached to a labeling substance that is selected from the group consisting of biotin, iminobiotin, digoxigenin, chemiluminescent dyes, and radioisotopes.

7. A fusion protein of the following formula:
P$^1$-C-(X)$_n$-W-X-X-X-W-(X)$_m$-C-P$^2$
wherein C-(X)$_n$-W-X-X-X-W-(X)$_m$-C  (I) (SEQ ID NO: 17)

is a human IgG binding peptide tag that is 11 to 16 amino acids in length,
wherein n and m are each an integer of 1 or more and the sum n+m is 4 or 5, wherein X-X-X in the formula contains no cysteine residue, and
wherein said human IgG binding peptide tag satisfies either or both of a) and b):
 a) (X)$_n$-W in the formula is Za-G-Y-W (SEQ ID NO: 18); and
 b) W-(X)$_m$ in the formula is W-G-L-Zb (SEQ ID NO: 19)
wherein Za and Zb are each 0, 1, or more amino acid residues,
wherein either of P$^1$ and P$^2$ is present, but P$^1$ and P$^2$ are not both present at the same time,
wherein P$^1$, when present, is bonded to the N-terminus of the human IgG binding peptide tag C-(X)$_n$-W-X-X-X-W-(X)$_m$-C (SEQ ID NO:17),
wherein P$^2$, when present, is bonded to the C-terminus of the human IgG binding peptide tag C-(X)$_n$-W-X-X-X-W-(X)$_m$-C (SEQ ID NO:17),
and wherein P$^1$ and P$^2$ each represents a protein.

8. A solid phase support, on which the peptide tag according to claim 1 is immobilized.

9. A method for determining the presence of human IgG or an Fc region-containing fragment thereof in a sample, comprising the steps a) to c):
 a) contacting a sample with acid to produce an acid-treated sample;
 b) contacting the acid-treated sample with the peptide tag according to claim 1; and
 c) measuring a binding affinity produced in the step b) between the peptide tag and human IgG or an Fc region-containing fragment thereof, wherein the binding affinity having a dissociation constant of 0.1 nM to 50 nM indicates the presence of human IgG or an Fc region-containing fragment thereof in a sample.

10. The method according to claim 9, wherein the binding affinity is measured by surface plasmon resonance analysis.

11. A method for purifying human IgG or an Fc region-containing fragment thereof in a sample, comprising the steps a) and b):
 a) contacting the peptide tag according to claim 1 with an acid-treated sample containing human IgG or an Fc region-containing fragment thereof, thereby binding human IgG or an Fc region-containing fragment thereof in the sample to the peptide tag; and
 b) separating the human IgG or the Fc region-containing fragment thereof, which is bound to the peptide tag in the step a), from the sample.

12. A method for removing an acid-denatured human IgG or Fc region-containing fragment thereof from a sample, comprising the steps a) and b):
 a) contacting the peptide tag according to claim 1 with a sample containing acid-denatured human IgG or an Fc region-containing fragment thereof; and
 b) removing human IgG or an Fc region-containing fragment thereof bound to the peptide tag prepared by the step a), from the sample.

13. A method for purifying a protein, comprising the steps a) to c):

a) producing a fusion protein according to claim 7, and then preparing a sample containing the fusion protein;

b) contacting the sample prepared by step a) with acid-treated human IgG or an Fc region-containing fragment thereof, thereby binding the fusion protein to the human IgG or Fc region-containing fragment thereof; and c) separating the fusion protein, which is bound to the human IgG or Fc region-containing fragment thereof in the step b), from the sample.

* * * * *

SEQUENCE LISTING

<160> NUMBER OF SEQ ID NOS: 25

<210> SEQ ID NO 1
<211> LENGTH: 11
<212> TYPE: PRT
<213> ORGANISM: Artificial Sequence -continued

```
<220> FEATURE:
<223> OTHER INFORMATION: Description of Artificial Sequence: synthetic
      peptide

<400> SEQUENCE: 1

Cys Gly Tyr Trp Arg Ser Glu Trp Gly Leu Cys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 2

Cys Thr Gly Phe Trp Glu Arg Glu Trp Gly Leu Cys
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 3

Cys Leu Tyr Trp Pro Arg Leu Trp Gly Leu Cys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 4

Cys Thr Gly Tyr Trp Pro Lys Ala Trp Gly Leu Cys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 5

Cys Tyr Trp Ala Val Arg Trp Gly Leu Leu Gly Cys
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 6

Cys Gly Tyr Trp Ala Asp Val Trp Gln Ile His Cys
1               5                   10
```

```
<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 7

Gly Cys Gly Tyr Trp Arg Ser Glu Trp Gly Leu Cys Gly
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 8

Gly Cys Thr Gly Phe Trp Glu Arg Glu Trp Gly Leu Cys Gly
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 9

Gly Cys Thr Gly Tyr Trp Pro Lys Ala Trp Gly Leu Cys Gly
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 10

Gly Cys Gly Tyr Trp Arg Ser Gln Trp Gly Leu Cys Gly
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 11

Gly Cys Thr Gly Tyr Trp Pro Arg Ala Trp Gly Leu Cys Gly
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 12
```

-continued

Gly Ser Gly Tyr Trp Arg Ser Glu Trp Gly Leu Ser Gly
1               5                   10

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: synthetic
      primer

<400> SEQUENCE: 13
ggagctgtcg tattccagtc                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: synthetic
      primer

<400> SEQUENCE: 14
aacccctcaa gacccgttta                                               20

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 15

Asp Cys Ala Trp His Leu Gly Glu Leu Val Trp Cys Thr
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: misc_feature
<222> LOCATION: (4)..(6)
<223> OTHER INFORMATION: Xaa can be any naturally occurring amino acid

<400> SEQUENCE: 16

Gly Tyr Trp Xaa Xaa Xaa Trp Gly Leu
1               5

<210> SEQ ID NO 17
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(5)
<223> OTHER INFORMATION: At least one amino acid must be present and up
      to three amino acids may be absent
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(9)

```
<223> OTHER INFORMATION: Xaa can be any naturally occurring amino acid,
      except cysteine
<220> FEATURE:
<221> NAME/KEY: misc_feature
<222> LOCATION: (11)..(14)
<223> OTHER INFORMATION: At least one amino acid must be present and up
      to three amino acids may be absent
<220> FEATURE:
<221> NAME/KEY: misc_feature
<222> LOCATION: (11)..(14)
<223> OTHER INFORMATION: Xaa can be any naturally occurring amino acid

<400> SEQUENCE: 17

Cys Xaa Xaa Xaa Xaa Trp Xaa Xaa Xaa Trp Xaa Xaa Xaa Xaa Cys
1               5                   10                  15

<210> SEQ ID NO 18
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa may be absent
<220> FEATURE:
<221> NAME/KEY: misc_feature
<222> LOCATION: (1)..(1)
<223> OTHER INFORMATION: Xaa, if present, can be any naturally occurring
      amino acid and may be preceded by one or more naturally occurring
      amino acids

<400> SEQUENCE: 18

Xaa Gly Tyr Trp
1

<210> SEQ ID NO 19
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa may be absent
<220> FEATURE:
<221> NAME/KEY: misc_feature
<222> LOCATION: (4)..(4)
<223> OTHER INFORMATION: Xaa, if present, can be any naturally occurring
      amino acid, and may be followed by one or more naturally occurring
      amino acids

<400> SEQUENCE: 19

Trp Gly Leu Xaa
1

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(6)
<223> OTHER INFORMATION: Xaa can be any naturally occurring amino acid

<400> SEQUENCE: 20

Gly Tyr Trp Xaa Xaa Xaa Trp Gly Leu
1               5
```

```
<210> SEQ ID NO 21
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(4)
<223> OTHER INFORMATION: Xaa can be any naturally occurring amino acid

<400> SEQUENCE: 21

Trp Xaa Xaa Xaa Trp
1               5

<210> SEQ ID NO 22
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa may be present or absent; if present, Xaa
      can be any naturally occurring amino acid
<220> FEATURE:
<221> NAME/KEY: misc_feature
<222> LOCATION: (4)..(4)
<223> OTHER INFORMATION: Xaa is Phe or Tyr
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa is Gly or Gln
<220> FEATURE:
<221> NAME/KEY: misc_feature
<222> LOCATION: (11)..(11)
<223> OTHER INFORMATION: Xaa is Leu or Ile
<220> FEATURE:
<221> NAME/KEY: misc_feature
<222> LOCATION: (12)..(13)
<223> OTHER INFORMATION: Xaa may be present or absent; if present, Xaa
      can be any naturally occurring amino acid

<400> SEQUENCE: 22

Cys Xaa Xaa Xaa Trp Xaa Xaa Xaa Trp Xaa Xaa Xaa Xaa Cys
1               5                   10

<210> SEQ ID NO 23
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa, if present, can be any naturally occurring
      amino acid
<220> FEATURE:
<221> NAME/KEY: misc_feature
<222> LOCATION: (3)..(6)
<223> OTHER INFORMATION: At least one amino acid must be present and up
      to three amino acids may be absent
<220> FEATURE:
<221> NAME/KEY: misc_feature
<222> LOCATION: (3)..(6)
<223> OTHER INFORMATION: Xaa, if present, can be any naturally occurring
      amino acid
<220> FEATURE:
<221> NAME/KEY: misc_feature
```

```
<222> LOCATION: (8)..(10)
<223> OTHER INFORMATION: Xaa can be any naturally occurring amino acid
      except cysteine
<220> FEATURE:
<221> NAME/KEY: misc_feature
<222> LOCATION: (12)..(15)
<223> OTHER INFORMATION: At least one amino acid must be present and up
      to three amino acids may be absent
<220> FEATURE:
<221> NAME/KEY: misc_feature
<222> LOCATION: (12)..(15)
<223> OTHER INFORMATION: Xaa, if present, can be any naturally occurring
      amino acid
<220> FEATURE:
<221> NAME/KEY: misc_feature
<222> LOCATION: (17)..(17)
<223> OTHER INFORMATION: Xaa, if present, can be any naturally occurring
      amino acid

<400> SEQUENCE: 23

Xaa Cys Xaa Xaa Xaa Xaa Trp Xaa Xaa Xaa Trp Xaa Xaa Xaa Xaa Cys
1               5                   10                  15

Xaa

<210> SEQ ID NO 24
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(11)
<223> OTHER INFORMATION: Up to two amino acids may be absent
<220> FEATURE:
<221> NAME/KEY: misc_feature
<222> LOCATION: (2)..(11)
<223> OTHER INFORMATION: Xaa, if present, can be any naturally occurring
      amino acid

<400> SEQUENCE: 24

Cys Xaa Xaa Xaa Xaa Xaa Xaa Xaa Xaa Xaa Xaa Cys
1               5                   10

<210> SEQ ID NO 25
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(14)
<223> OTHER INFORMATION: Up to two amino acids may be absent
<220> FEATURE:
<221> NAME/KEY: misc_feature
<222> LOCATION: (5)..(14)
<223> OTHER INFORMATION: Xaa, if present, can be any naturally occurring
      amino acid
<220> FEATURE:
<221> NAME/KEY: misc_feature
<222> LOCATION: (16)..(18)
<223> OTHER INFORMATION: Xaa can be any naturally occurring amino acid

<400> SEQUENCE: 25

Xaa Xaa Xaa Cys Xaa Xaa Xaa Xaa Xaa Xaa Xaa Xaa Xaa Xaa Cys Xaa
1               5                   10                  15

Xaa Xaa
```